(12) United States Patent
Daniels et al.

(10) Patent No.: US 8,597,298 B2
(45) Date of Patent: Dec. 3, 2013

(54) PROXIMAL REAMER

(75) Inventors: David W. Daniels, Winona Lake, IN (US); Jonathan E. Carr, Warsaw, IN (US); Barry A. Schnieders, Plymouth, IN (US); Larry G. McCleary, Warsaw, IN (US); Gabriel M. Surma, Winona Lake, IN (US)

(73) Assignee: DePuy Synthes Products, LLC, Raynham, MA (US)

( * ) Notice: Subject to any disclaimer, the term of this patent is extended or adjusted under 35 U.S.C. 154(b) by 1766 days.

(21) Appl. No.: 11/529,799

(22) Filed: Sep. 29, 2006

(65) Prior Publication Data

US 2008/0161811 A1 Jul. 3, 2008

(51) Int. Cl.
*A61B 17/00* (2006.01)

(52) U.S. Cl.
USPC ........................................................... 606/80

(58) Field of Classification Search
USPC ....... 606/60, 62, 65, 67, 79, 80, 86 R, 88, 96, 606/98; 623/20.14, 20.35, 20.36
See application file for complete search history.

(56) References Cited

U.S. PATENT DOCUMENTS

| | | | |
|---|---|---|---|
| 650,795 A | 5/1900 | Maxwell et al. |
| 1,029,402 A | 6/1912 | Ritter |
| 3,177,507 A | 4/1965 | Becker et al. |
| 3,633,583 A | 1/1972 | Fishbein |
| 3,810,312 A | 5/1974 | Carson |
| 4,004,581 A | 1/1977 | Heimke et al. |
| 4,116,200 A | 9/1978 | Braun et al. |
| 4,473,070 A | 9/1984 | Matthews et al. |
| 4,601,289 A | 7/1986 | Chiarizzio et al. |
| 4,658,808 A | 4/1987 | Link |
| 4,716,894 A | 1/1988 | Lazzeri et al. |
| 4,738,256 A | 4/1988 | Freeman et al. |
| 4,777,942 A | 10/1988 | Frey et al. |
| 4,917,530 A | 4/1990 | Engelhardt et al. |
| 4,969,911 A | 11/1990 | Greene |
| 5,002,578 A | 3/1991 | Luman |
| 5,002,581 A | 3/1991 | Paxson et al. |

(Continued)

FOREIGN PATENT DOCUMENTS

| | | |
|---|---|---|
| DE | 3538654 A1 | 4/1987 |
| EP | 0206777 A2 | 12/1986 |

(Continued)

OTHER PUBLICATIONS

Paul, H. A., et al., "Development of a Surgical Robot for Cementless Total Hip Arthroplasty," Clinical Orthopaedics and Related Research 285, Dec. 1992, 57-66 (10 pages).

(Continued)

*Primary Examiner* — Sameh Boles
(74) *Attorney, Agent, or Firm* — Maginot, Moore & Beck, LLP

(57) ABSTRACT

A reamer for reaming a proximal portion of a cavity for use in implanting a joint prosthesis is provided. The reamer is used for cooperation with a proximal portion of an orthopaedic implant component. The reamer includes a body defining a cavity formed therein for receiving at least a portion of the orthopaedic implant component. The reamer also includes a plurality of cutting edges extending outwardly from the body. The edges are adapted for cooperation with bone. The reamer also includes a stem extending from an end of the body.

4 Claims, 45 Drawing Sheets

(56) References Cited

U.S. PATENT DOCUMENTS

| | | |
|---|---|---|
| 5,015,255 A | 5/1991 | Kuslich |
| 5,047,033 A | 9/1991 | Fallin |
| 5,053,037 A | 10/1991 | Lackey |
| 5,100,407 A | 3/1992 | Conrad et al. |
| 5,135,529 A | 8/1992 | Paxson et al. |
| 5,171,244 A | 12/1992 | Caspari et al. |
| 5,192,283 A | 3/1993 | Ling et al. |
| 5,197,989 A | 3/1993 | Hinckfuss et al. |
| 5,201,882 A | 4/1993 | Paxson |
| 5,207,680 A | 5/1993 | Dietz et al. |
| 5,228,459 A | 7/1993 | Caspari et al. |
| 5,263,498 A | 11/1993 | Caspari et al. |
| 5,304,181 A | 4/1994 | Caspari et al. |
| D346,979 S | 5/1994 | Stalcup et al. |
| 5,336,226 A | 8/1994 | McDaniel et al. |
| 5,342,363 A | 8/1994 | Richelsoph |
| 5,344,423 A | 9/1994 | Dietz et al. |
| 5,370,706 A | 12/1994 | Bolesky et al. |
| 5,372,209 A | 12/1994 | Raihert et al. |
| 5,387,218 A | 2/1995 | Meswania |
| 5,395,376 A | 3/1995 | Caspari et al. |
| D357,315 S | 4/1995 | Dietz |
| 5,403,320 A | 4/1995 | Luman et al. |
| 5,415,659 A | 5/1995 | Lee et al. |
| 5,468,243 A | 11/1995 | Halpern |
| 5,470,336 A | 11/1995 | Ling et al. |
| 5,474,559 A | 12/1995 | Bertin et al. |
| 5,486,180 A | 1/1996 | Dietz et al. |
| 5,496,324 A | 3/1996 | Barnes |
| 5,507,815 A | 4/1996 | Wagner et al. |
| 5,507,824 A | 4/1996 | Lennox |
| 5,507,830 A | 4/1996 | DeMane et al. |
| 5,507,833 A | 4/1996 | Bohn |
| 5,527,316 A | 6/1996 | Stone et al. |
| 5,534,005 A | 7/1996 | Tokish, Jr. et al. |
| 5,540,694 A | 7/1996 | DeCarlo, Jr. et al. |
| 5,569,255 A | 10/1996 | Burke |
| 5,593,411 A | 1/1997 | Stalcup et al. |
| 5,601,563 A | 2/1997 | Burke et al. |
| 5,601,567 A | 2/1997 | Swajger et al. |
| 5,607,269 A | 3/1997 | Dowd et al. |
| 5,607,431 A | 3/1997 | Dudasik et al. |
| 5,643,271 A | 7/1997 | Sederholm et al. |
| 5,645,607 A | 7/1997 | Hickey |
| 5,653,714 A | 8/1997 | Dietz et al. |
| 5,658,349 A | 8/1997 | Brooks et al. |
| 5,683,395 A | 11/1997 | Mikhail |
| 5,697,932 A | 12/1997 | Smith et al. |
| 5,702,487 A | 12/1997 | Averill et al. |
| 5,728,128 A | 3/1998 | Crickenberger et al. |
| 5,743,915 A | 4/1998 | Bertin et al. |
| 5,752,972 A | 5/1998 | Hoogeboom |
| 5,755,803 A | 5/1998 | Haines et al. |
| 5,766,261 A | 6/1998 | Neal et al. |
| 5,769,855 A | 6/1998 | Bertin et al. |
| 5,776,200 A | 7/1998 | Johnson et al. |
| 5,792,143 A | 8/1998 | Samuelson et al. |
| 5,810,827 A | 9/1998 | Haines et al. |
| 5,810,829 A | 9/1998 | Elliott et al. |
| 5,810,830 A | 9/1998 | Noble et al. |
| 5,853,415 A | 12/1998 | Bertin et al. |
| 5,858,020 A | 1/1999 | Johnson et al. |
| 5,860,969 A | 1/1999 | White et al. |
| 5,860,981 A | 1/1999 | Bertin et al. |
| 5,876,459 A | 3/1999 | Powell |
| 5,879,354 A | 3/1999 | Haines et al. |
| 5,879,391 A | 3/1999 | Slamin |
| 5,906,644 A | 5/1999 | Powell |
| 5,908,423 A | 6/1999 | Kashuba et al. |
| 5,919,195 A | 7/1999 | Wilson et al. |
| 5,935,172 A | 8/1999 | Ochoa et al. |
| 5,951,606 A | 9/1999 | Burke |
| 5,957,925 A | 9/1999 | Cook et al. |
| 5,968,049 A | 10/1999 | Da Rold |
| 5,976,145 A | 11/1999 | Kennefick, III |
| 5,976,147 A | 11/1999 | LaSalle et al. |
| 5,976,188 A | 11/1999 | Dextradeur et al. |
| 5,993,455 A | 11/1999 | Noble |
| 6,045,556 A | 4/2000 | Cohen |
| 6,056,754 A | 5/2000 | Haines et al. |
| 6,071,311 A | 6/2000 | O'Neil et al. |
| 6,080,162 A | 6/2000 | Dye et al. |
| 6,090,146 A | 7/2000 | Rozow, III et al. |
| 6,117,138 A | 9/2000 | Burrows et al. |
| 6,120,507 A | 9/2000 | Allard et al. |
| 6,126,694 A | 10/2000 | Gray, Jr. |
| 6,159,214 A | 12/2000 | Michelson |
| 6,162,226 A | 12/2000 | DeCarlo, Jr. et al. |
| 6,179,877 B1 | 1/2001 | Burke |
| 6,193,259 B1 | 2/2001 | Rupard |
| 6,193,759 B1 | 2/2001 | Ro et al. |
| 6,197,064 B1 | 3/2001 | Haines et al. |
| 6,197,065 B1 | 3/2001 | Martin et al. |
| 6,206,884 B1 | 3/2001 | Masini |
| 6,224,605 B1 | 5/2001 | Anderson et al. |
| 6,238,435 B1 | 5/2001 | Meulink et al. |
| 6,258,093 B1 | 7/2001 | Edwards et al. |
| 6,258,095 B1 | 7/2001 | Lombardo et al. |
| 6,258,097 B1 | 7/2001 | Cook et al. |
| 6,270,502 B1 | 8/2001 | Stulberg |
| 6,287,342 B1 | 9/2001 | Copf et al. |
| 6,318,651 B1 | 11/2001 | Spiering |
| 6,319,286 B1 | 11/2001 | Fernandez et al. |
| 6,332,886 B1 | 12/2001 | Green et al. |
| 6,355,068 B1 | 3/2002 | Doubler et al. |
| 6,361,563 B2 | 3/2002 | Terrill-Grisoni et al. |
| 6,432,110 B1 | 8/2002 | Richelsoph |
| 6,432,141 B1 | 8/2002 | Stocks et al. |
| 6,440,139 B2 | 8/2002 | Michelson |
| 6,508,841 B2 | 1/2003 | Martin et al. |
| 6,517,581 B2 | 2/2003 | Blamey |
| RE38,058 E | 4/2003 | Fallin |
| 6,589,285 B2 | 7/2003 | Penenberg |
| 6,663,616 B1 | 12/2003 | Roth et al. |
| 6,676,706 B1 | 1/2004 | Mears et al. |
| 6,692,530 B2 | 2/2004 | Doubler et al. |
| 6,702,854 B1 | 3/2004 | Cheal et al. |
| 6,740,090 B1 | 5/2004 | Cragg et al. |
| 6,770,100 B2 | 8/2004 | Draenert |
| 6,824,552 B2 | 11/2004 | Robison et al. |
| 6,846,314 B2 | 1/2005 | Shapira |
| 6,875,218 B2 | 4/2005 | Dye et al. |
| 6,883,217 B2 | 4/2005 | Barrette et al. |
| 6,905,515 B1 | 6/2005 | Gilbertson |
| 6,911,048 B2 | 6/2005 | Fernandez et al. |
| 6,949,101 B2 | 9/2005 | McCleary et al. |
| 7,001,392 B2 | 2/2006 | McGovern |
| 7,008,420 B2 | 3/2006 | Okada |
| 7,074,224 B2 | 7/2006 | Daniels et al. |
| 7,641,658 B2 | 1/2010 | Shaolian et al. |
| 2001/0001121 A1 | 5/2001 | Lombardo et al. |
| 2001/0007957 A1* | 7/2001 | Martin et al. ............. 623/23.17 |
| 2001/0016779 A1 | 8/2001 | Lubinus |
| 2001/0034526 A1 | 10/2001 | Kuslich et al. |
| 2002/0183758 A1 | 12/2002 | Middleton et al. |
| 2003/0093080 A1 | 5/2003 | Brown et al. |
| 2003/0109882 A1 | 6/2003 | Shirado et al. |
| 2003/0114933 A1 | 6/2003 | Bouttens et al. |
| 2003/0130740 A1 | 7/2003 | Stocks et al. |
| 2003/0171756 A1 | 9/2003 | Fallin et al. |
| 2003/0171816 A1 | 9/2003 | Scifert et al. |
| 2003/0187449 A1 | 10/2003 | McCleary et al. |
| 2003/0204269 A1 | 10/2003 | Gerbec et al. |
| 2003/0220698 A1 | 11/2003 | Mears et al. |
| 2004/0015239 A1 | 1/2004 | Beguec |
| 2004/0054419 A1 | 3/2004 | Serra et al. |
| 2004/0064186 A1 | 4/2004 | McCleary et al. |
| 2004/0092951 A1 | 5/2004 | Serra et al. |
| 2004/0122437 A1 | 6/2004 | Dwyer et al. |
| 2004/0122440 A1 | 6/2004 | Daniels et al. |
| 2004/0122525 A1 | 6/2004 | Daniels et al. |
| 2004/0147933 A1 | 7/2004 | McGovern |
| 2004/0172138 A1 | 9/2004 | May et al. |
| 2004/0267266 A1 | 12/2004 | Daniels et al. |

(56) References Cited

U.S. PATENT DOCUMENTS

| | | | |
|---|---|---|---|
| 2004/0267267 A1* | 12/2004 | Daniels et al. ............... | 606/80 |
| 2004/0267372 A1 | 12/2004 | Vanasse et al. | |
| 2005/0004679 A1 | 1/2005 | Sederholm et al. | |
| 2005/0154331 A1 | 7/2005 | Christie et al. | |
| 2005/0222572 A1 | 10/2005 | Chana | |
| 2005/0234461 A1 | 10/2005 | Burdulis, Jr. et al. | |
| 2005/0288676 A1 | 12/2005 | Schnieders et al. | |
| 2006/0015110 A1 | 1/2006 | Pepper | |

FOREIGN PATENT DOCUMENTS

| | | |
|---|---|---|
| EP | 0206777 A3 | 12/1987 |
| EP | 0206777 B1 | 5/1990 |
| EP | 0511244 A4 | 4/1993 |
| EP | 0595956 A4 | 8/1994 |
| EP | 0661023 A2 | 7/1995 |
| EP | 0726063 A1 | 8/1996 |
| EP | 0842639 A2 | 5/1998 |
| EP | 0842639 A3 | 6/1998 |
| EP | 0 861 635 A2 | 9/1998 |
| EP | 0595956 B1 | 9/1998 |
| EP | 0511244 B1 | 10/1998 |
| EP | 0861635 A3 | 11/1998 |
| EP | 1084680 A2 | 3/2001 |
| EP | 0661023 B1 | 8/2001 |
| EP | 1 201 191 A1 | 5/2002 |
| EP | 0861635 B1 | 7/2002 |
| EP | 1323395 A2 | 7/2003 |
| EP | 1348384 A2 | 10/2003 |
| EP | 1348384 A3 | 11/2003 |
| EP | 1369089 A2 | 12/2003 |
| EP | 0842639 B1 | 2/2004 |
| EP | 1369089 A3 | 6/2004 |
| EP | 1493407 A2 | 1/2005 |
| EP | 1084680 B1 | 3/2005 |
| EP | 1493407 A3 | 4/2005 |
| EP | 1323395 A3 | 8/2005 |
| EP | 1 263 334 B1 | 10/2005 |
| EP | 1591084 A1 | 11/2005 |
| FR | 2737107 A1 | 7/1995 |
| FR | 2828397 A1 | 8/2001 |
| GB | 2250441 A | 6/1992 |
| JP | 5212069 A | 8/1993 |
| JP | 2000210314 A | 8/2000 |
| JP | 2003339724 A | 12/2003 |
| JP | 2006501917 A | 1/2006 |
| WO | 1991010408 A1 | 7/1991 |
| WO | 1992010138 A1 | 6/1992 |
| WO | WO 93/01769 | 2/1993 |
| WO | 1994012123 A1 | 6/1994 |
| WO | 94/27507 | 12/1994 |
| WO | 1998015739 A1 | 4/1998 |
| WO | 2002102254 A2 | 12/2002 |
| WO | 03015642 A1 | 2/2003 |
| WO | 2002102254 A3 | 5/2003 |
| WO | 2002102254 B1 | 6/2003 |
| WO | 03/065906 A2 | 8/2003 |
| WO | 2003082159 A1 | 10/2003 |
| WO | 2003092513 A1 | 11/2003 |
| WO | 2003094698 A2 | 11/2003 |
| WO | 2003094803 A1 | 11/2003 |
| WO | 2004032767 A1 | 4/2004 |
| WO | 2003094698 A3 | 6/2004 |

OTHER PUBLICATIONS

Depuy Orthopaedics, Inc., "S-Rom Modular Hip System, Minimally Invasive Calcar Miller Surgical Technique", 0612-04-503, DePuy Orthopaedics, Inc., 2004 (12 pages).

Translation of Japan Patent Office Notification of Reasons for Refusal in corresponding Japanese patent application JP 2007-254157, mailed May 15, 2012 (4 pages).

European Search Report and European Search Opinion in corresponding application EP 07253847.3, dated Jan. 28, 2008 (7 pages).

European Search Report and European Search Opinion in corresponding application EP 10170706.5, dated Sep. 21, 2010 (6 pages).

European Search Report and European Search Opinion in corresponding application EP 09168260.9, dated Jan. 13, 2010 (6 pages).

Translation of Chinese Patent Office First Office Action in corresponding Chinese patent application CN 200710170103.2, issued Apr. 26, 2010 (9 pages).

* cited by examiner

PROXIMAL REAMER

TECHNICAL FIELD OF THE INVENTION

The present invention relates generally to the field of orthopaedics, and more particularly, to an implant for use in arthroplasty.

BACKGROUND OF THE INVENTION

Patients who suffer from the pain and immobility caused by osteoarthritis and rheumatoid arthritis have an option of joint replacement surgery. Joint replacement surgery is quite common and enables many individuals to function properly when it would not be otherwise possible to do so. Artificial joints are usually comprised of metal, ceramic and/or plastic components that are fixed to existing bone.

Such joint replacement surgery is otherwise known as joint arthroplasty. Joint arthroplasty is a well-known surgical procedure by which a diseased and/or damaged joint is replaced with a prosthetic joint. In a typical total joint arthroplasty, the ends or distal portions of the bones adjacent to the joint are resected or a portion of the distal part of the bone is removed and the artificial joint is secured thereto.

There are known to exist many designs and methods for manufacturing implantable articles, such as bone prostheses. Such bone prostheses include components of artificial joints such as elbows, hips, knees and shoulders.

Currently in total hip arthroplasty, a major critical concern is the instability of the joint. Instability is associated with dislocation. Dislocation is particularly a problem in total hip arthroplasty.

Factors related to dislocation include surgical technique, implant design, implant positioning and patient related factors. In total hip arthroplasty, implant systems address this concern by offering a series of products with a range of lateral offsets, neck offsets, head offsets and leg lengths. The combination of these four factors affects the laxity of the soft tissue. By optimizing the biomechanics, the surgeon can provide a patient a stable hip much more resistant to dislocation.

In order to accommodate the range of patient arthropathy metrics, a wide range of hip implant geometries are currently manufactured by DePuy Orthopaedics, Inc., the assignee of the current application, and by other companies. In particular, the S-ROM® total hip systems offered by DePuy Orthopaedics, Inc. include three offsets, three neck lengths, four head lengths and one leg length adjustment. The combination of all these biomechanic options is rather complex.

Anteversion of a total hip system is closely linked to the stability of the joint. Improper anteversion can lead to dislocation and patient dissatisfaction. Anteversion control is important in all hip stems. However, it is a more challenging issue with the advent of stems with additional modularity.

The prior art has provided for some addressing of the anteversion problem. For example, the current S-ROM® stems have laser markings on the medial stem and the proximal sleeve. This marking enables the surgeon to measure relative alignment between these components. Since the sleeve has infinite anteversion, it is not necessarily oriented relative to a bony landmark that can be used to define anteversion. In fact, the current sleeves are sometimes oriented with the spout pointing directly laterally into the remaining available bone.

When a primary or index total joint arthroplasty fails, a revision procedure is performed in which the index devices (some or all) are removed. Quite often the remaining bone is significantly compromised compared to a primary hip procedure. Significant bone loss is observed, often with a lack of bone landmarks typically used for alignment.

In a common step in the surgical procedure known as total hip arthroplasty, a trial or substitute stem is first implanted into the patient. The trial is utilized to verify the selected size and shape of the implant in situ on the patient and the patient is subjected to what is known as a trial reduction. This trial reduction represents moving the joint, including the trial implant through selected typical motions for that joint. Current hip instruments provide a series of trials of different sizes to help the surgeon assess the fit and position of the implant. Trials, which are also known as provisionals, allow the surgeon to perform a trial reduction to assess the suitability of the implant and the implant's stability prior to final implant selection. In order to reduce inventory costs and complexity, many trialing systems are modular. For example, in the Excel™ Instrument System, a product of DePuy Orthopaedics, Inc., there is a series of broaches and a series of neck trials that can be mixed and matched to represent the full range of implants. There is a single fixed relationship between a broach and a neck trial, because these trials represent a system of monolithic stem implants.

Likewise, in the current S-ROM® instrument systems provided by DePuy Orthopaedics, Inc., there are neck trials, proximal body trials, distal stem trials, head trials and sleeve trials. By combining all of these components, the implant is represented. Since the S-ROM® stem is modular and includes a stem and a sleeve, the angular relationship or relative anteversion between the neck and the sleeve is independent and represented by teeth mating between the neck and the proximal body trial. The proximal body trial has fixed transverse bolts that are keyed to the sleeve in the trialing for straight, primary stems. The long stem trials do not have the transverse bolts and are thus not rotationally stable during trial reduction and therefore are not always used by the surgeon.

With the introduction of additional implant modularity, the need for independent positioning of the distal stem, proximal body and any sleeve that comprise the implants is required. Currently bowed, monolithic stems are offered with a fixed amount of anteversion, typically 15 degrees.

Currently available implants, trials and instruments result in a lengthy surgical procedure. This lengthy surgical procedure includes the steps of preparing the canal, removing the instruments to prepare the canal, implanting trials, performing a trial reduction and then implanting the prosthesis. This lengthy procedure increases the risk of the patient's surgical complications.

When utilizing currently available instruments, trials and surgical procedures, the surgeon must perform the trial reduction on the patient before the surgeon has any feedback regarding the appropriateness of the trial and the positioning of the trial in the body. Adjustments in the positioning and selection of the trial and resultant implants thus become difficult and time consuming to perform.

Utilizing the current instruments, the trials and implants all need to be properly located and selected to obtain the optimum results for the patient. The positioning of the trial with respect to the femur and the implant with respect to the trial currently allow for much variation from procedure to procedure.

To optimize patient outcomes, orthopaedic surgery preferably conserves as much of the resected bone as possible. Current surgical procedures require that sufficient bone be resected and removed by instruments in the proximal bone to provide for clearance for the proximal trial and the proximal implant. Thus, under current techniques, material must be removed proximally on the bone to provide for the variety of positions that may be optimum for the patient.

US Patent Application Publication No. 20040122439 entitled "ADJUSTABLE BIOMECHANICAL TEMPLATING & RESECTION INSTRUMENT AND ASSOCIATED METHOD", US Patent Application Publication No. 20040122437 entitled "ALIGNMENT DEVICE FOR MODULAR IMPLANTS AND METHOD" and US Patent Application Publication No. 20040122440 entitled "INSTRUMENT AND ASSOCIATED METHOD OF TRIALING FOR MODULAR HIP STEMS" are hereby incorporated in their entireties by reference.

When performing hip arthroplasty using bowed stems, the distal canal is prepared with a reamer and the bowed step is installed in the reamed cavity. The longitudinal centerline of the proximal body of the implant is not in alignment with the centerline of the distal stem due to the fact that the distal stem is bowed. The reamer that prepares the distal cavity can not remove bone to provide clearance to the proximal body in a precise manner to minimize bone removal, due to the fact that the proximal body centerline of the implant is not in alignment with the distal stem centerline. Either additional material must be removed by the distal reamer from the proximal bone to allow for this non-alignment, or additional material must be removed by other means, for example by an osteotome. Either method requires additional bone removal that is not clinically desired.

While the prior art has attempted to reduce the steps in surgical techniques and improve the ability to precisely remove bone to prepare the bone for receiving a proximal component, the need remains for a system and apparatus to reduce the steps in surgical techniques utilizing distal reamers and proximal bodies for modular implants.

The present invention is directed to alleviate at least some of the problems with the prior art.

SUMMARY OF THE INVENTION

The design of the present invention gives the surgeon the ability to remove proximal bone after the distal implant has been implanted utilizing the fixed position of the implant to support a tool to remove the proximal bone.

The present invention provides a reamer that utilizes the distal implant in the long bone as a guide for proximally reaming the long bone.

After a long bone, for example a hip, has been resected, you must ream distally to prepare canal for the distal stem implant in a modular distal stem and proximal body implant assembly. This reaming is done using a tapered reamer. The distal stem implant has a 3° bend to accommodate for the natural interior bow of the femoral canal in long distal stem implant configurations used in revision arthroplasty. Because of the 3° bend, proximal reaming must be separately performed to remove the bone not removed by the distal tapered reamer. Once the implant has been implanted, the surgeon may, utilizing the present invention, use the proximal end or tapered portion of the distal stem implant as a pilot shaft for the proximal reamer. A protective sleeve may be placed over the tapered portion of the distal stem component of the implant to prevent damage to the distal stem component while the proximal reaming is being performed. The next step for the surgeon, after the proximal reaming, would be to proceed with implanting the proximal body implant or a proximal body trial. A trial reduction is then performed and, if a trial reduction includes a proper implant/trial assembly selection, the corresponding implant is then inserted onto the distal stem implant.

According to one embodiment of the present invention, there is provided a reamer for reaming a proximal portion of a cavity for use in implanting a joint prosthesis. The reamer cooperates with a proximal portion of an orthopaedic implant stem. The reamer includes a body defining a cavity formed in the body for receiving at least a portion of the orthopaedic implant stem. The reamer also includes a plurality of cutting edges extending outwardly from the body. The edges are adapted for cooperation with bone. The reamer also includes a stem extending from an end of the body.

According to another embodiment of the present invention there is provided a reamer assembly for reaming a cavity for use in implanting an orthopaedic implant stem of a joint prosthesis. The reamer cooperates with a proximal portion of an orthopaedic implant stem. The reamer assembly includes a sleeve that fits over the proximal portion of the orthopaedic implant stem. The sleeve defines an outer periphery of the sleeve. The reamer assembly also includes a reamer having a body defining a cavity formed in the body for receiving at least a portion of the outer periphery of the sleeve. The reamer also has a plurality of cutting edges extending outwardly from the body. The edges are adapted for cooperation with bone. The reamer also has a stem extending from an end of the body.

According to yet another embodiment of the present invention there is provided a sleeve for use with an orthopaedic implant stem and a proximal reamer. The sleeve fits over the proximal portion of the orthopaedic implant stem. The sleeve defines an outer periphery of the sleeve.

According to a further embodiment of the present invention, there is provided a kit for use in joint arthroplasty. The kit includes a proximal orthopaedic implant stem and a sleeve that fits over the proximal portion of the orthopaedic implant stem. The sleeve defines an outer periphery of the sleeve. The kit also includes a reamer. The reamer has a body defining a cavity formed in the body for receiving at least a portion of the orthopaedic implant stem. The reamer also includes a plurality of cutting edges extending outwardly from the body. The edges are adapted for cooperation with bone. The reamer also includes a stem extending from an end of the body.

According to a further embodiment of the present invention, there is provided a method for providing joint arthroplasty. The method includes the steps of resecting an end portion of a long bone and preparing a central longitudinal opening in a medullary canal of the long bone. The method also includes the steps of providing a prosthetic stem component and installing the prosthetic stem component into the opening in a medullary canal. The method also includes the steps of providing a reamer including an opening for receiving the prosthetic stem component and positioning the reamer onto prosthetic stem component with the opening of the reamer positioned at least partially over the prosthetic stem component. The method also includes the steps of reaming a portion of the long bone with the reamer, removing the reamer; and installing a prosthetic body component onto the prosthetic stem component.

According to a further embodiment of the present invention, there is provided a method for providing joint arthroplasty comprising. The method includes the steps of resecting an end portion of a long bone and preparing a central longitudinal opening in a medullary canal of the long bone. The method also includes the steps of providing a prosthetic stem component and installing the prosthetic stem component into the opening in a medullary canal. The method also includes the steps of installing a sleeve onto the prosthetic stem component and providing a reamer including an opening for receiving the prosthetic stem component. The method also includes the steps of positioning the reamer onto the sleeve and reaming a portion of the long bone with the reamer. The method also includes the steps of removing the reamer and installing a prosthetic body component onto the prosthetic stem component.

The technical advantages of the present invention include the ability to reduce the number of steps in the surgical technique necessary to perform orthopedic surgery, for example hip implant surgery. For example, according to one aspect of the present invention a method for providing joint arthroplasty is provided. The method includes the steps of resecting an end portion of a long bone, preparing a central longitudinal opening in the canal, providing a prosthetic stem component, and installing the stem component into the opening. The method also includes the step for providing a reamer for receiving the prosthetic stem component. The reamer is positioned at least partially over the prosthetic stem component. By placing the reamer over the prosthetic stem component a separate tool is not required to guide the reamer and a prosthetic trial or other component is not required to be positioned in the canal to provide the support for the reamer. Thus the present invention provides for a reduction in the number of steps in the surgical technique for joint arthroplasty.

The technical advantages of the present invention further include a reduction in the number of instruments required to perform a joint arthroplasty, a reduced number of instruments in the instrument tray and a reduction in the related costs of the instruments. For example, and according to another aspect of the present invention, a method and apparatus for providing joint arthroplasty is provided in which the distal stem implant is implanted into the reamed bone canal without the use of a distal stem trial. Therefore, the instrument of a distal stem trial is not required in this aspect of the present invention. Thus the present invention provides for a reduced number of instruments required to perform the joint arthroplasty.

The technical advantages of the present invention further include the ability to remove bone proximally from the long bone after a distal stem implant is installed into the long bone of the patient. For example, according to another aspect of the present invention a method for performing joint arthroplasty is provided which includes providing a prosthetic stem component which is positioned in the canal of the long bone and providing a reamer for receiving the prosthetic stem component. A proximal reamer is positioned onto the prosthetic stem component and reams a proximal portion of the long bone. Thus the present invention provides for removing bone proximally after a distal stem implant is installed.

The technical advantages of the present invention further include the ability to remove bone in a form that is eccentric with the center line of the distal canal with a reamer. For example, according to another aspect of the present invention a reamer assembly is provided for reaming a proximal portion of a cavity for use in implanting a proximal body implant of a modular joint prosthesis. The reamer cooperates with a proximal portion of the distal stem implant. The reamer assembly includes a proximal reamer and a sleeve that slips over the proximal portion of the distal stem implant. The sleeve may snap into a cavity of the proximal reamer. The orthopedic implant stem has a proximal portion that is non-linear with the distal portion of the implant stem. Thus the present invention provides the ability to remove bone that is eccentric with the distal canal with a reamer. Reaming of the proximal portion of the long bone may be better than broaching the proximal portion in that bone may be too sclerotic or too weak and fragile to absorb the impaction force from broaching.

The technical advantages of the present invention further include the ability to use the implant as an implant shaft for reaming. For example, according to another aspect of the present invention a reamer assembly for reaming a proximal portion of a cavity for a joint prosthesis is provided. The assembly includes a sleeve that fits over the orthopedic stem and a reamer that is fitted over the sleeve and is used to prepare a proximal portion of the long bone. Thus the present invention provides for ability to use the implant as a pilot shaft for the reamer.

The technical advantages of the present invention further include the ability to perform in situa proximal body trialing on top of a distal implant stem. For example, according to yet another aspect of the present invention a method providing joint arthroplasty is provided. The method includes the steps of resecting an end portion of the long bone, preparing an opening in the canal and providing a distal stem component. The distal stem component is installed into the canal and a reamer, including an opening for receiving the proximal portion of the distal stem component, is positioned over the stem with the reamer reaming in situa the proximal portion of the long bone for receiving the proximal body component. A proximal body implant component or a proximal body trial component may be positioned over the prosthetic distal stem implant component and a trial performed on top of the distal prosthetic stem implant component. Thus, the present invention provides for the performing in situa a proximal body trialing on top of a distal implant component.

Other technical advantages of the present invention will be readily apparent to one skilled in the art from the following figures, descriptions and claims.

BRIEF DESCRIPTION OF THE DRAWINGS

For a more complete understanding of the present invention and the advantages thereof, reference is now made to the following description taken in connection with the accompanying drawings, in which:

FIG. 3I is a plan view of a sleeve having a protrusion on the outer periphery of the sleeve according to another embodiment of the present invention;

FIG. 4I is a plan view of a implant/sleeve/pin assembly with the guide pin of FIG. 4H assembled onto the implant/sleeve assembly of FIG. 4;

DETAILED DESCRIPTION OF THE INVENTION

Embodiments of the present invention and the advantages thereof are best understood by referring to the following descriptions and drawings, wherein like numerals are used for like and corresponding parts of the drawings.

Figure 1:
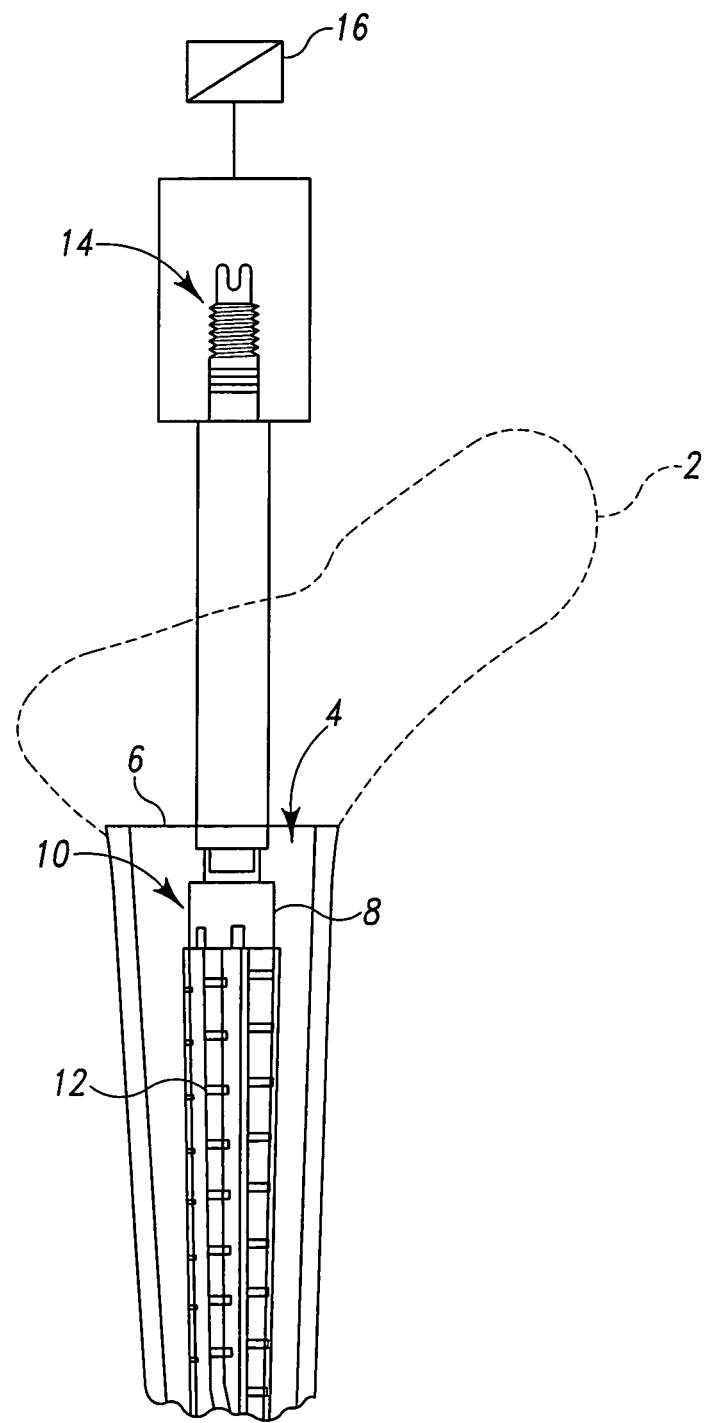
FIG. 1 is a plan view of a reamer in position in a long bone for preparing a bone canal for receiving a long bone prosthetic stem.

Referring now to FIG. 1 a long bone or femur 2 for use with the present invention is shown. The femur 2 includes an intermedullary canal 4 into which the prosthesis of the present invention may be inserted. The femur 2 is resected along resection line 6 by, for example, a power tool, for example, a saw. The resecting of the long bone or femur 2 exposes the intermedullary canal 4 of femur 2. A reamer 8 that may be a standard commercially available reamer is positioned in the intermedullary canal 4 of the long bone 2 to form cavity 10 for receiving an orthopedic joint implant. The reamer 8 includes a plurality of longitudinally extending flutes 12 which are used to remove bone and other biological matter from the intermedullary canal 4 to form the cavity 10. The reamer 8 may be rotated by use of a connector 14 positioned on the reamer 8. The connector 14 may be any standard connector for example a Hudson or an A-O connector. The connector 14 is used to connect to a power tool 16 for rotating the reamer 8. The power tool 16 may be any standard power tool. It should be appreciated that the reamer 8 may be rotated through the use of the connector 14 by a hand tool for example a "T" shaped handle.

Figure 2:
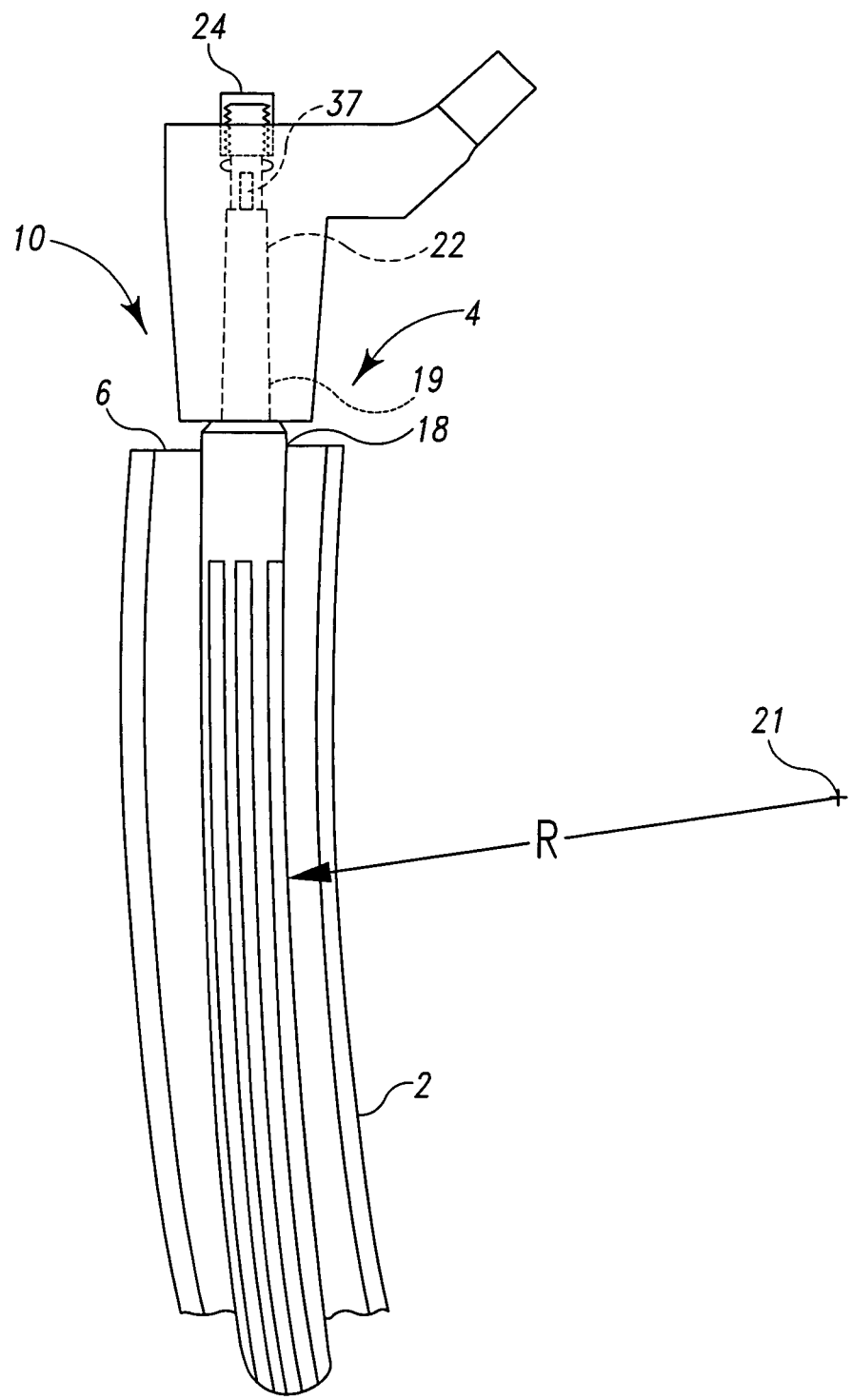
FIG. 2 is a plan view of a curved long bone distal stem implant in position in the canal prepared by the reamer of FIG. 1 for use with the present invention.

Referring now to FIG. 2, a distal implant stem 18 is shown fitted into the cavity 10 formed in the intermedullary canal 4 of the long bone or femur 2. The distal implant stem 18 may, as is shown in FIG. 2, be in the form of a curved or bent stem. The natural femur has a curve that may best be replicated in an implant component, particularly when the distal implant stem has a particularly long length, such as is used in a revision arthroplasty. The distal implant stem shape may be defined by a radius R extending from origin 21. The curved or bent portion of stem 18 may be located mostly distally on the stem 18. The distal implant stem includes an external tapered proximal portion 20 and a connector in the form of external threads 24 located proximally from the tapered proximal portion 20. The resection line 6 may generally correspond to the position at which the stem 18, when implanted, begins the external tapered portion 20 of the stem 18.

Figure 2A:
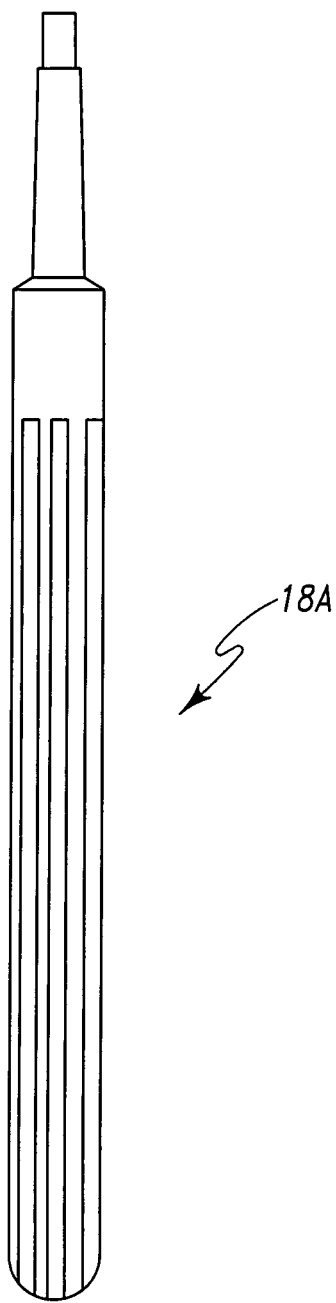
FIG. 2A is a plan view of a straight long bone distal stem implant in position in the canal prepared by the reamer of FIG. 1 for use with the present invention.

Referring now to FIG. 2A, it should be appreciated that the stem may be in the form of a straight or cylindrical stem 18A which does not include a curved or bent portion. The use of the proximal reamer in the present invention with such a cylindrical stem 18A may provide for bone removal for receiving the proximal body that is precise and that minimizes bone removal in comparison with other methods of removing bone for receiving the proximal body.

Figure 3:
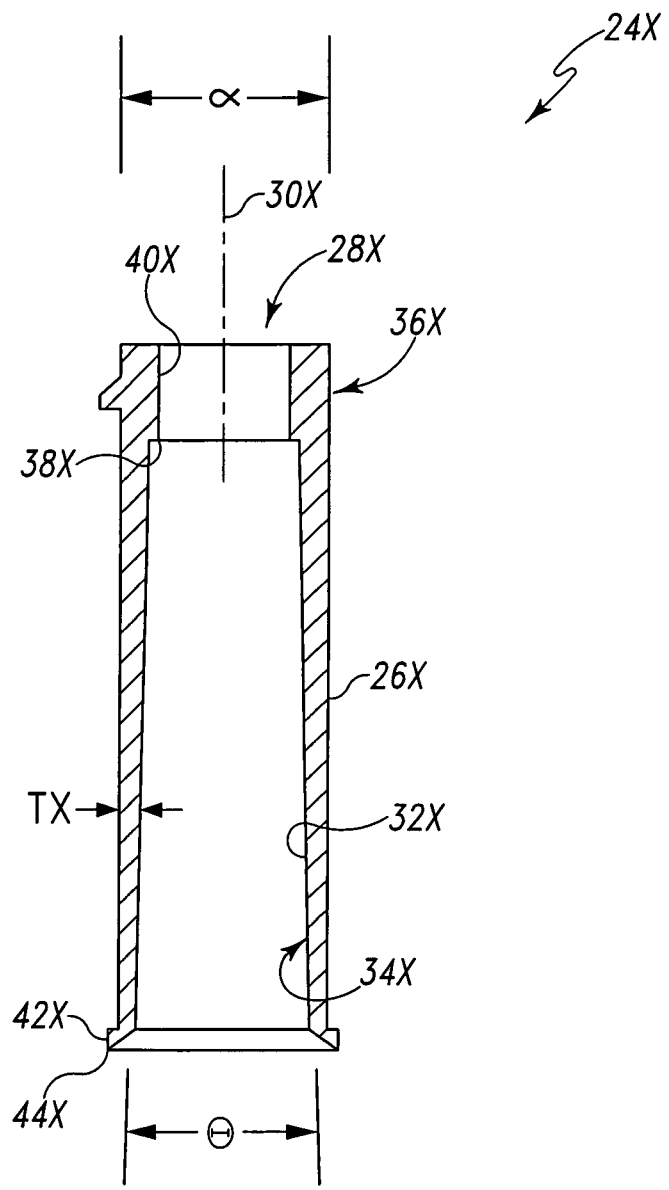
FIG. 3 is a plan view of a sleeve for use on the distal long bone stem of FIG. 2, according to an embodiment of the present invention.

According to the present invention, and referring now to FIG. 3, a sleeve 24X for use with distal implant stems, for example stem 18 of FIG. 2, is shown. The sleeve 24X is used with a proximal reamer 58C (See FIG. 5C). The sleeve 24X, as shown in FIG. 3, is fitable over the tapered proximal portion 20 of the distal implant stem 18. The sleeve 24X defines an outer periphery 26X of the sleeve 24X. As shown in FIG. 3, the sleeve 24X may be hollow and may include a cavity 28X extending longitudinally along sleeve center line 30X. The cavity 28X may define an inner periphery 32X of the sleeve 24X. The inner periphery 32X of the sleeve 24X may have any shape that mates with external periphery 19 of the tapered proximal portion 20 of the stem 18 (See FIG. 2).

Referring again to FIG. 2, the stem 18 includes the tapered proximal portion 20 as well as the threaded portion 22. Similarly, and referring to FIG. 3, the inner periphery 32X includes tapered portion 34X to mate with tapered portion 20 of the stem 18. Also, the inner periphery 32X of the sleeve 24X includes a threaded cylindrical portion 36X which mates with internal threads 25 formed on the stem 18 (See FIG. 2).

The tapered portion 34X and the cylindrical portion 36X define a step or shoulder 38X positioned between the cylindrical portion 36X and the tapered portion 34X of the sleeve 24X. The sleeve 24X may include the outer periphery 26X having a shape compatible to that of the proximal reamer (See FIG. 5C). The outer periphery 26X may, as is shown in FIG. 3, be tapered and defined by an included angle $\alpha$. The included angle $\alpha$ may be designed such that the sleeve 24X may have a wall thickness T which is generally uniform. Thus the tapered portion 34X of the internal periphery 32X of the sleeve 24X may be defined by and include an included angle $\theta$ which is similar to the included angle $\alpha$. As shown in FIG. 3, the internal angle $\alpha$ is slightly smaller than the included angle $\theta$.

Preferably the sleeve 24X is fixedly secured to stem 18 of FIG. 2 so that wear or damage does not occur to the tapered proximal portion 20 of the stem 18. Thus the sleeve 24X may include a feature for assuring that the stem 18 is fixedly secured to the sleeve 24X when assembled together. The angle $\alpha\alpha$ of the internal periphery at the tapered portion 34X may be designed such that it provides for a locking taper with the tapered portion 20 of the stem 18. Alternatively, the cylindrical portion 36X of the inner periphery 32X may include a feature of, for example, internal threads 40X show in phantom, which may alternatively be used to thread the sleeve 24X into engagement with external threads 23 on the stem 18.

Figure 3A:
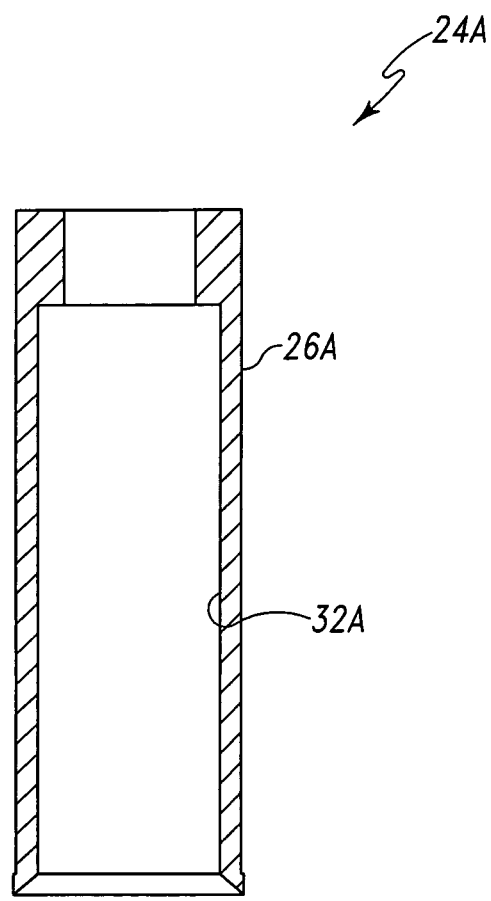
FIG. 3A is a plan view of a sleeve with a cylindrical bore and a cylindrical outer periphery according to another embodiment of the present invention.

Referring now to FIG. 3A, an alternate embodiment of the present invention is shown as sleeve 24A. Sleeve 24A is like sleeve 24 of FIG. 3 except that sleeve 24A includes an outer periphery 26A and an inner periphery 32A that are both cylindrical. The sleeve 24A is suitable for use with reamers having a cylindrical profiled driving surface.

Figure 3B:
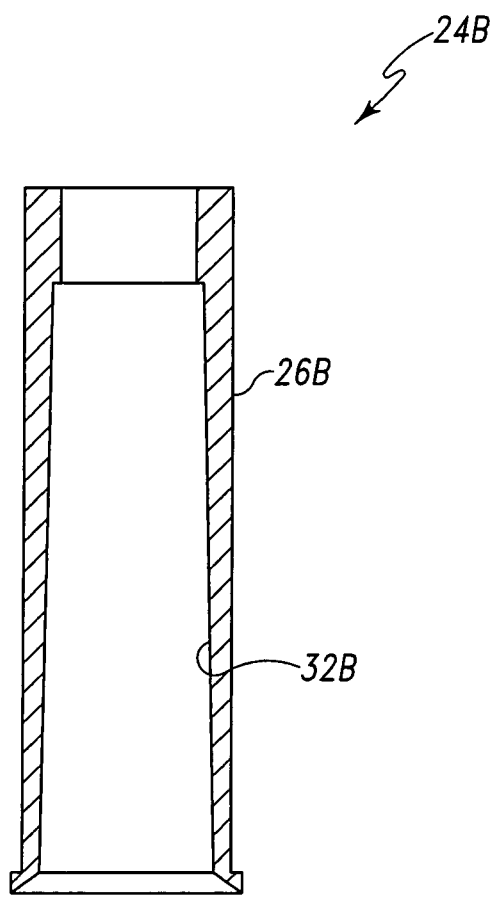
FIG. 3B is a plan view of a sleeve with a cylindrical bore and a tapered outer periphery according to another embodiment of the present invention.

Referring now to FIG. 3B, another embodiment of the present invention is shown as shown as sleeve 24B. The sleeve 24B is similar to the sleeve 24 of FIG. 3 except that the sleeve 24B includes an outer periphery 26B which is cylindrical and an inner periphery 32B which is tapered. It should be appreciated that the sleeve 24B of FIG. 3B may have a uniform configuration of the inner periphery 32B with no step or shoulder, as well as, a simple cylindrical shape of outer periphery 26B.

The sleeve 24 may include an annular external ring or lip 42 which extends outwardly from outer periphery 26 at lower end 44 of the sleeve 24. The lip 42 may serve to prevent the outer periphery 26 of the sleeve 24 to be permanently taper locked onto the proximal reamer.

While it is desirable to have the sleeve 24 be rigidly fixed to the distal implant 18 when the proximal reamer is used with the sleeve 24, such rigid engagement of the sleeve 24 to the implant stem 18 may be acquired by an interference fit between the inner periphery 32 of the sleeve 24 and the tapered external portion 20 of the stem 18 if the components are cylindrical or tapered locked if not.

It should also be appreciated that to assure the locking of the sleeve 24 to the stem 18, the sleeve 24 may include a locking or securing feature 46 that cooperates with a connection feature 56 on the stem 18 to assure the rigidity of the sleeve 24 against the stem 18.

Figure 3C:
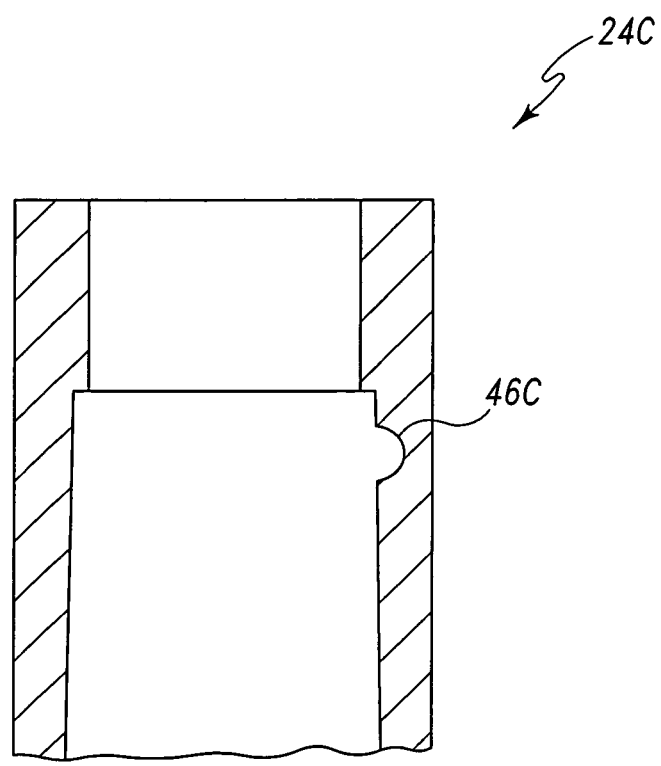
FIG. 3C is a partial plan view of a recess in the bore of a sleeve to mate with a protrusion on the distal long bone stem according to another embodiment of the present invention.

As shown in FIG. 3C, a sleeve 24C is shown which is similar to the sleeve 24 of FIG. 3 except that the sleeve 24C includes the sleeve/stem securing feature 46C in the form of an indentation. The indentation 46C may mate with a complimentary protrusion extending from the outer periphery 26 of the external tapered portion 20 of the stem 18 (see FIG. 2).

Figure 3D:
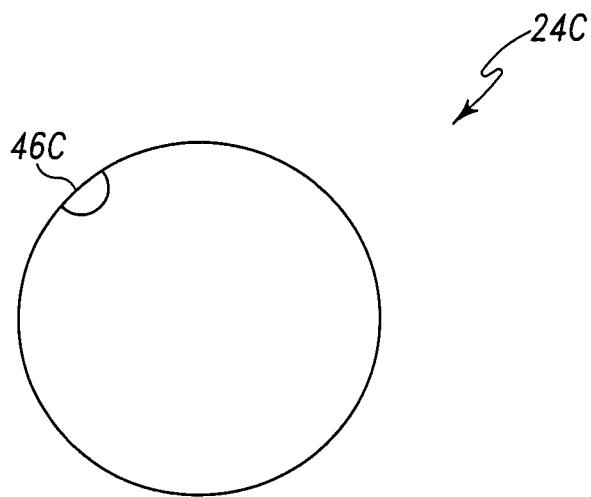
FIG. 3D is an end view of the sleeve of FIG. 3C showing the recess in the bore of the sleeve.

Referring now to FIG. 3D, the sleeve 24C may include a solitary indent 46C as shown in FIG. 3D.

Figure 3E:
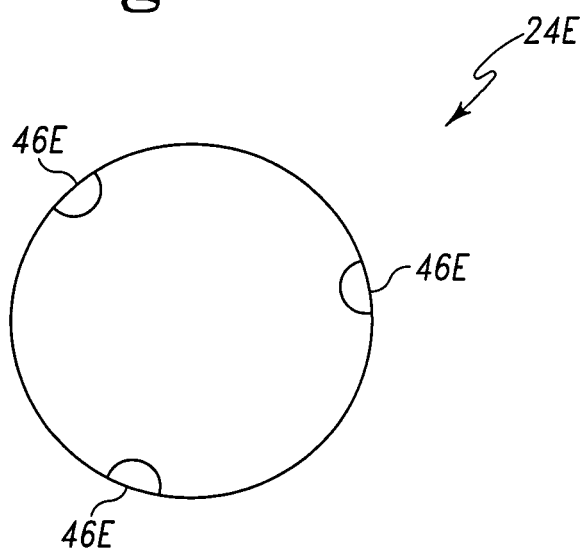
FIG. 3E is an end view of a sleeve having three spaced apart recesses in the bore of the sleeve according to another embodiment of the present invention.

Referring now to FIG. 3E, another embodiment of the present invention is shown as sleeve 24E. Sleeve 24E is like sleeve 24C of FIGS. 3C and 3D except that the sleeve 24E includes more than one indent, for example, three spaced apart indents 46E.

Figure 3F:
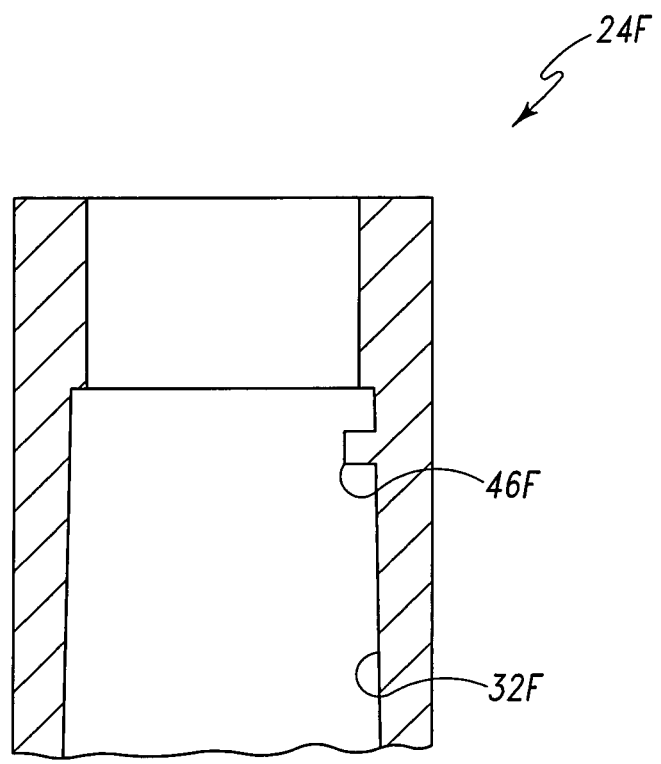
FIG. 3F is a partial plan view of a protrusion in the bore of the sleeve to mate with a recess on the distal long bone stem according to another embodiment of the present invention.
Figure 3G:
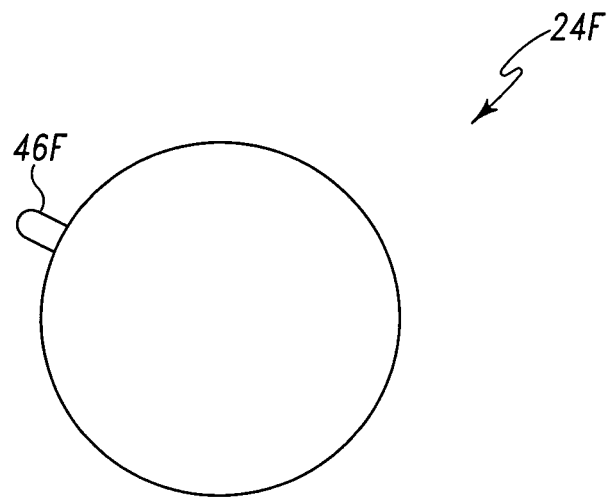
FIG. 3G is an end view of the sleeve of FIG. 3F showing the protrusion in the bore of the sleeve.

Referring now to FIGS. 3F and 3G, yet another embodiment of the present invention is shown as sleeve 24F. Sleeve 24F is similar to sleeve 24 of FIG. 3 except that the sleeve 24F includes a sleeve/stem securing feature in the form of a protrusion 46F extending inwardly from inner periphery 32F of the sleeve 24F. As shown in FIG. 3G, the protrusion 46F is a solitary protrusion. The protrusion 46F of FIGS. 3F and 3G may mate with an indent 56F formed on the external tapered portion 20F of the stem 18F of FIG. 4F.

Figure 3H:
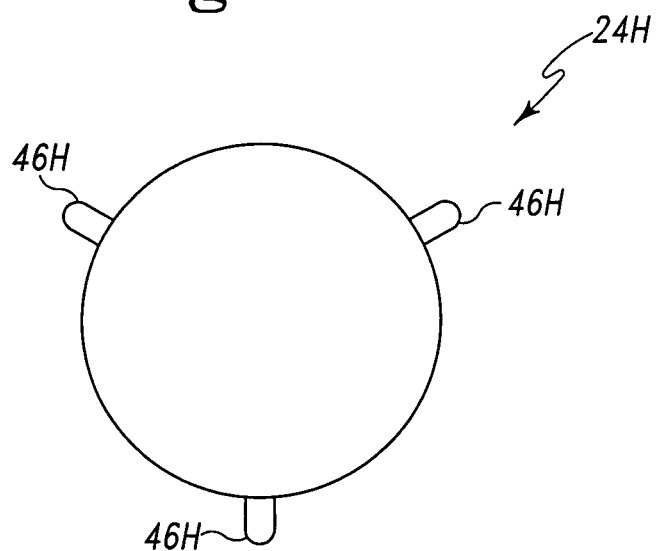
FIG. 3H is an end view of a sleeve having three spaced apart protrusions in the bore of the sleeve according to another embodiment of the present invention.
Figure 3:
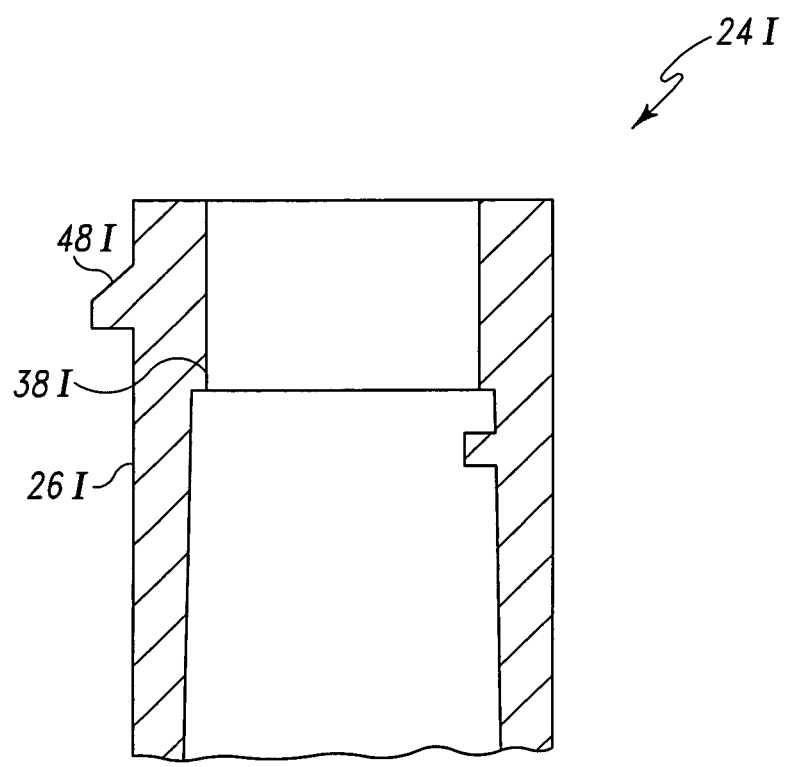

Referring now to FIG. 3H, yet another embodiment of the present invention is shown as sleeve 24H. The sleeve 24H is like the sleeve 24F except that the sleeve 24H includes three spaced apart protrusions 46H.

Referring now to FIG. 3I, yet another embodiment of the present invention is shown as sleeve 24I. The sleeve 24I is similar to sleeve 24 of FIG. 3 except that the sleeve 24I includes a sleeve/proximal reamer securing feature in the form of a protrusion 48I positioned near shoulder 38I of the sleeve 24. The protrusion 48I extends outwardly from outer periphery 26I of the sleeve 24I. The protrusion 48I serves to mate with an indent on the proximal reamer so that when the proximal reamer is extracted from the stem 18, the sleeve 24I remains with the proximal reamer and does not need to be separately removed from the stem 18 (see FIG. 2).

The protrusion 48I may have any suitable shape and may as shown in FIG. 3I be tapered downwardly to make the engagement of the protrusion into the opening easier in the downward direction of the reamer and to assure that the sleeve 24 is removed with the proximal reamer. This feature reduces surgical procedure steps and saves time in the operating room.

Figure 3J:
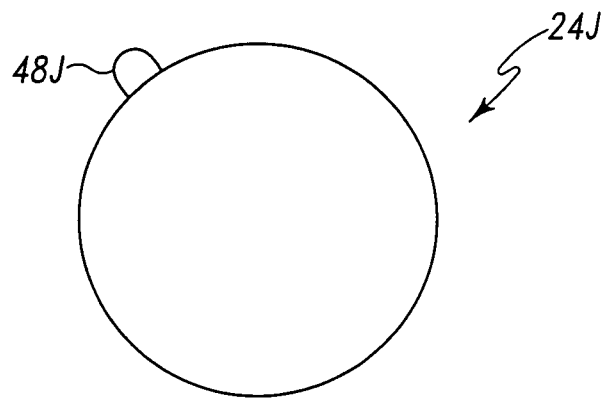
FIG. 3J is an end view of the sleeve of FIG. 3I showing the protrusion on the periphery of the sleeve.

Referring now to FIG. 3J, the protrusion 48I of the sleeve 24I may be a solitary protrusion.

Figure 3K:
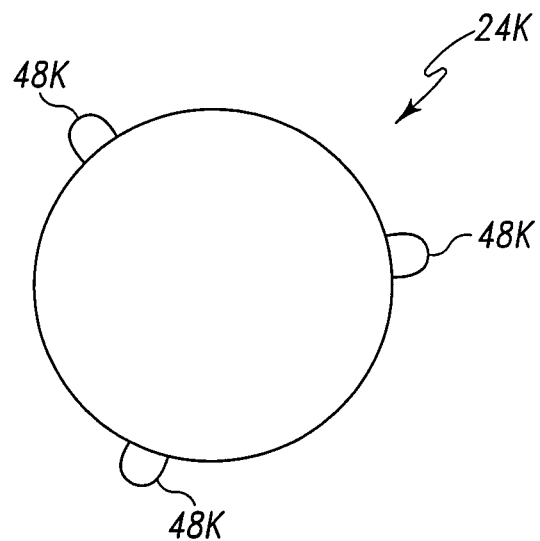
FIG. 3K is an end view of a sleeve having three spaced apart protrusions on the periphery of the sleeve according to another embodiment of the present invention.

Referring now to FIG. 3K, yet another embodiment of the present invention is shown as sleeve 24K. The sleeve 24K includes a protrusion 48K extending outwardly from external periphery 26K of the sleeve 24K. It should be appreciated as shown in FIG. 3K that three separate spaced apart protrusions 48K may be utilized with complimentary indents formed in the proximal reamer (see FIG. 4).

Figure 3L:
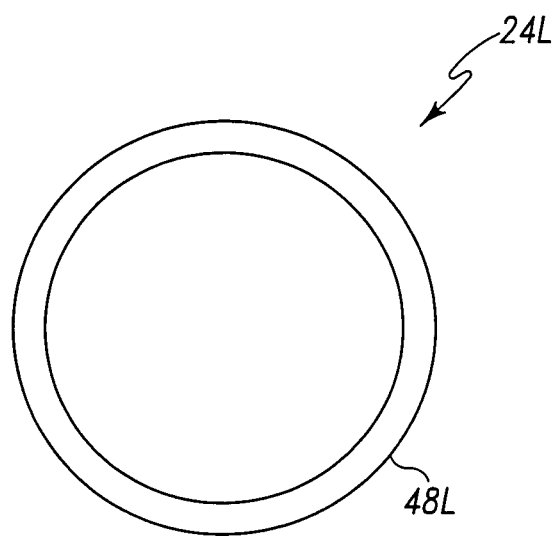
FIG. 3L is an top view of a sleeve having a rib or ring on the periphery of the sleeve according to another embodiment of the present invention.

Referring now to FIG. 3L, the protrusion 48I of the sleeve 24I may be a solitary protrusion that extends around the periphery of the sleeve to form a ring or lip.

Figure 3M:
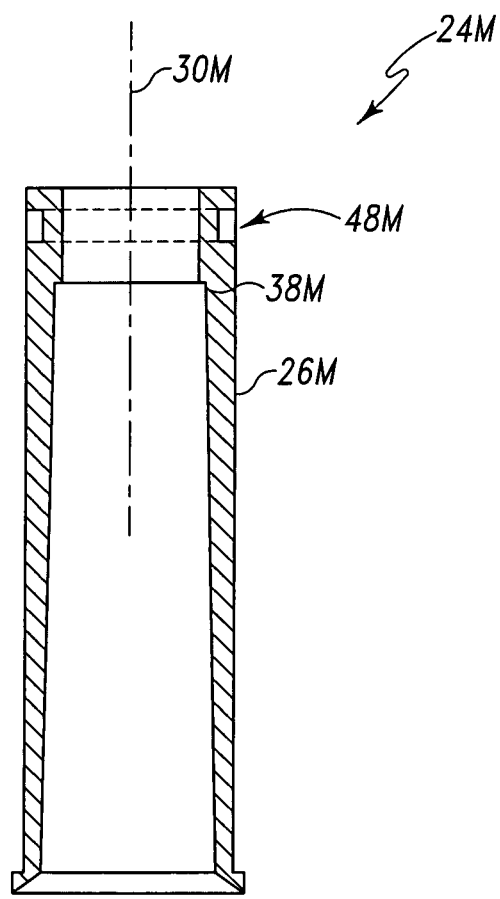
FIG. 3M is a plan view of a sleeve having a groove on the outer periphery of the sleeve according to another embodiment of the present invention.

Referring now to FIG. 3M, the sleeve 24X is shown in greater detail. The sleeve 24X may include a sleeve reamer connection feature 48X in the form of an internal groove 48X extending inwardly from outer periphery 26X of the sleeve 24X. The groove 48X may be positioned anywhere along longitudinal axis central line 30X of the sleeve 24X, but preferably is located near the shoulder 38X of the sleeve 24X. The groove 48X serves to mate with a detent 88C formed in the proximal reamer 58C (See FIG. 7A). It should be appreciated that the feature 48X should provide for an ability to have relative rotation between the sleeve 24X and the proximal reamer 58C.

Figure 3N:
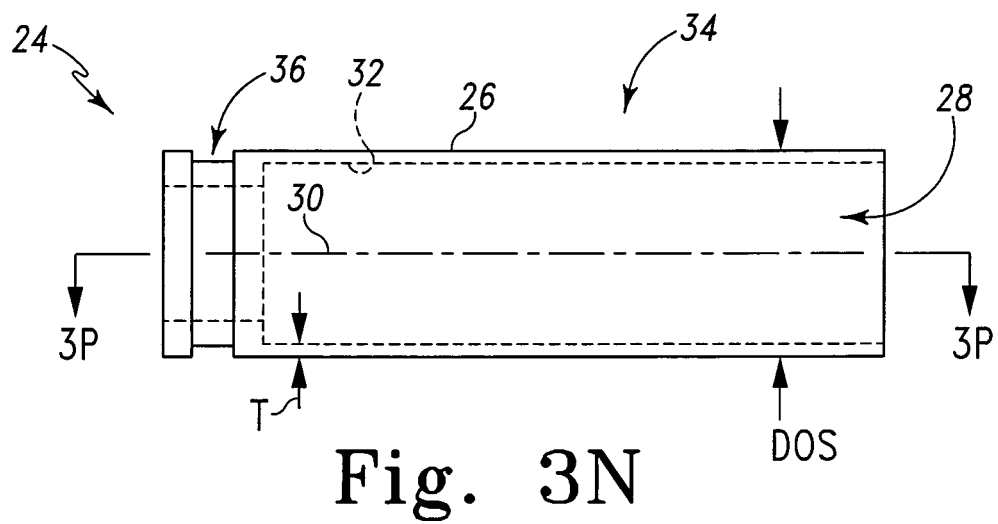
FIG. 3N is a plan view of a sleeve having a groove on the outer periphery of the sleeve with a cylindrical bore and with a cylindrical outside diameter according to another embodiment of the present invention.
Figure 3P:
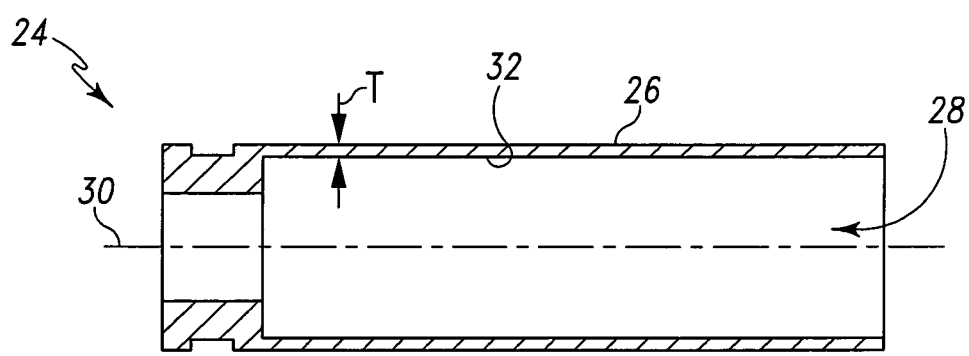
FIG. 3P is a cross sectional view along the lines 3P-3P in the direction of the arrows.
Figure 3Q:
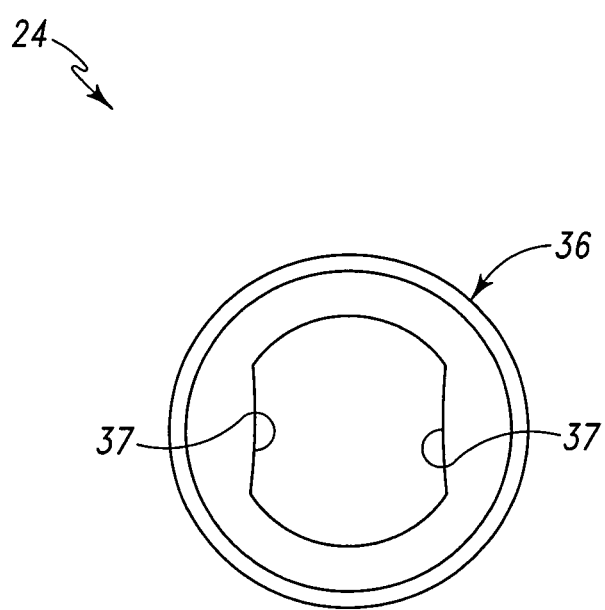
FIG. 3Q is a plan view of the sleeve of FIG. 3N.

According to the present invention, and referring now to FIGS. 3N, 3P and 3Q, a sleeve 24 for use with distal implant stems, for example stem 18 of FIG. 2, is shown. The sleeve 24 is used with a proximal reamer 58 (See FIG. 5). The sleeve 24, as shown in FIG. 3, is fitable over the tapered proximal portion 20 of the distal implant stem 18. The sleeve 24 defines an outer periphery 26 of the sleeve 24. As shown in FIG. 3, the sleeve 24 may be hollow and may include a cavity 28 extending longitudinally along sleeve center line 30. The cavity 28 may define an inner periphery 32 of the sleeve 24. The inner periphery 32 of the sleeve 24 may have any shape that mates with external periphery 19 of the tapered proximal portion 20 of the stem 18. The inner periphery 19 may be cylindrical and interferencely fit onto the tapered proximal portion 20 of the stem 18 of FIG. 2.

Referring again to FIG. 2, the stem 18 includes the tapered proximal portion 20 as well as the threaded portion 22. Similarly, and referring to FIGS. 3N, 3P and 3Q, the inner periphery 32 includes a distal cylindrical portion 34 to interferencely fit with tapered portion 20 of the stem 18. Also, the inner periphery 32 of the sleeve 24 includes a proximal cylindrical portion 36 with opposed double flats 37 which mates with opposed double flats 27 formed on the stem 18 (See FIG. 2).

Referring again to FIGS. 3N, 3P and 3Q, the distal cylindrical portion 34 and the proximal cylindrical portion 36 define a step or shoulder 38 positioned between the cylindrical portion 36 and the distal cylindrical portion 34 of the sleeve 24. The sleeve 24 may include the outer periphery 26 having a shape compatible to that of the proximal reamer (See FIG. 5). If the angle of the proximal reamer bore is small enough, the outer periphery 26 of the sleeve 24 may be cylindrical. The outer periphery 26 may, as is shown in FIG. 3, be cylindrical and defined by diameter DOS. The sleeve 24 may have a wall thickness T which is generally uniform. Thus distal cylindrical portion 34 of the internal periphery 32 of the sleeve 24 may be defined by wall thickness T.

Preferably the sleeve 24 is fixedly secured to stem 18 so that wear or damage does not occur to the tapered proximal portion 20 of the stem 18. Thus the sleeve 24 may include a feature for assuring that the stem 18 is fixedly secured to the sleeve 24 when assembled together. The distal cylindrical portion 34 of the internal periphery 32 of the sleeve 24 may be designed such that it provides for an interference fit with the tapered portion 20 of the stem 18. Alternatively, the cylindrical portion 36 of the inner periphery 32 may include a feature of, for example, internal threads (not shown), which may alternatively be used to thread the sleeve 24 into engagement with external threads 23 on the stem 18.

It should be appreciated that to assure the interference fit between the distal cylindrical portion 34 of the sleeve 24 and the tapered portion 20 of the stem 18 of the reamer 8, the sleeve may optionally have longitudinal slots (not shown) through the wall of the sleeve 24. The slot may be a single slot or a plurality of spaced apart slots. The slots may partially extend along the length of the sleeve 24 or may extend the fill length, splitting the sleeve 24. The slots permit additional interference fit.

Figure 4:
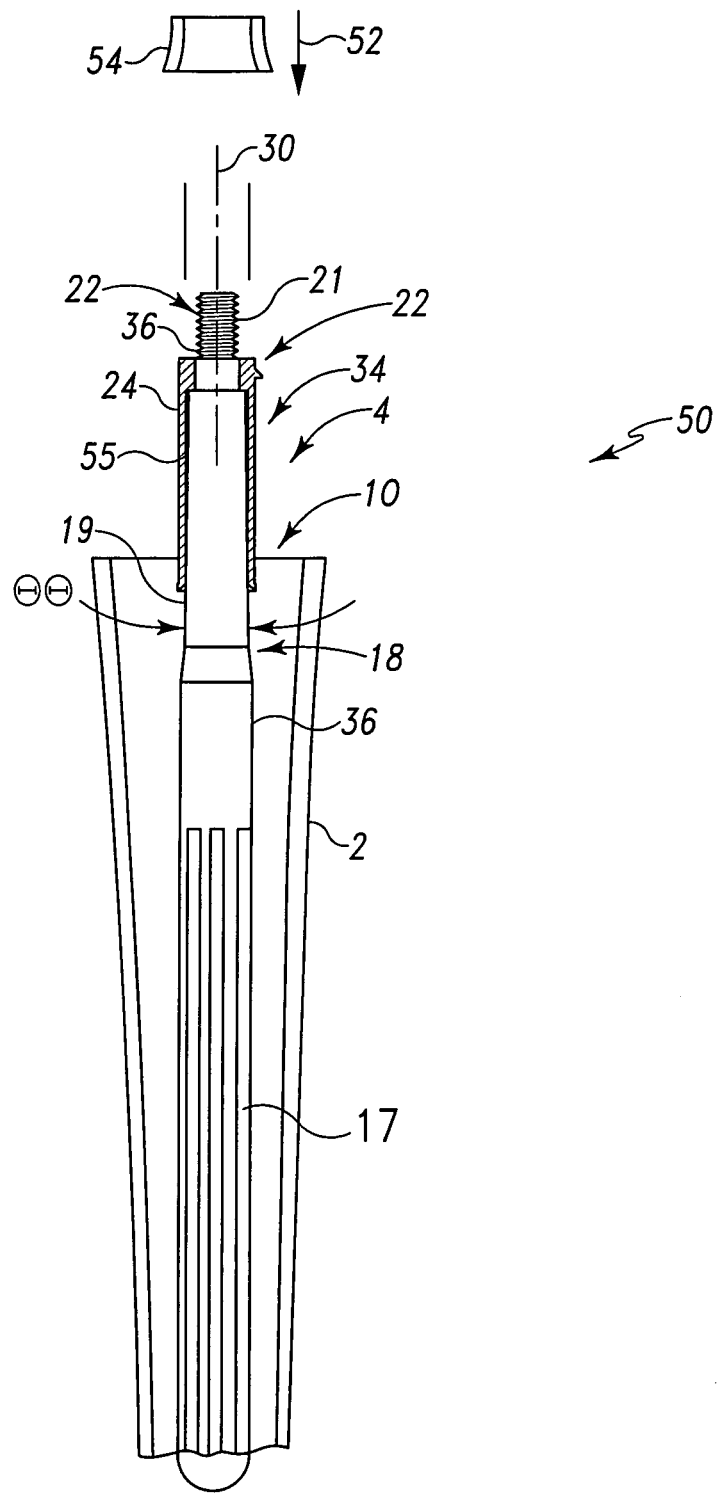
FIG. 4 is a plan view of the distal implant stem of FIG. 2 with the sleeve of FIG. 3M installed on the stem, to form a distal implant sleeve assembly.

According to the present invention and referring now to FIG. 4, an implant sleeve assembly 50 is shown. The implant sleeve assembly 50 includes the sleeve 24 of FIG. 3 positioned on the orthopedic implant stem 18 of FIG. 2. The orthopedic implant stem 18 is positioned in canal 4 of cavity 10 of soft or cancellous bone in the canal 4 of the femur 2. The sleeve 24 may be loaded onto the orthopedic implant stem 18 in the direction of arrow 52. The orthopedic implant stem 18 may be moved from loading position 54 as shown in phantom to the installed position 56 as shown in solid.

While the sleeve 24 may be installed in situa on the orthopedic implant stem 18 already installed into the canal 4 of the cavity 10 of the femur 2, it should be appreciated that the sleeve 24 may be preinstalled onto the orthopedic implant stem 18 prior to the performing of the surgery such that the sleeve 24 may protect external periphery 19 of the stem tapered portion 20 of the stem 18 during shipment and during the installation of the stem 18 into the cavity 10 of the canal 4 of the femur 2.

The sleeve 24 is preferably rigidly fitted against the orthopedic implant stem 18. The rigid connection of the sleeve 24 to the stem 18 may be accomplished by the fitting of the sleeve internal periphery 32 of the sleeve 24 against the external periphery 19 of the stem tapered portion 20 of the stem 18. The internal periphery 32 of the sleeve 24 may be cylindrical and may thus interferencely fit with the external periphery 19 of the stem tapered portion 20 of the orthopedic implant stem 18 defined by included angle θθ.

The orthopedic implant stem 18, like the sleeve 24, may include features to assure the rigid securement of the sleeve 24 to the stem 18. For example, and as shown in FIG. 4, the stem 18 may include a stem/sleeve connection feature 56 in the form of an interference fit for cooperation with the sleeve 24 (See FIG. 3).

Figure 4A:
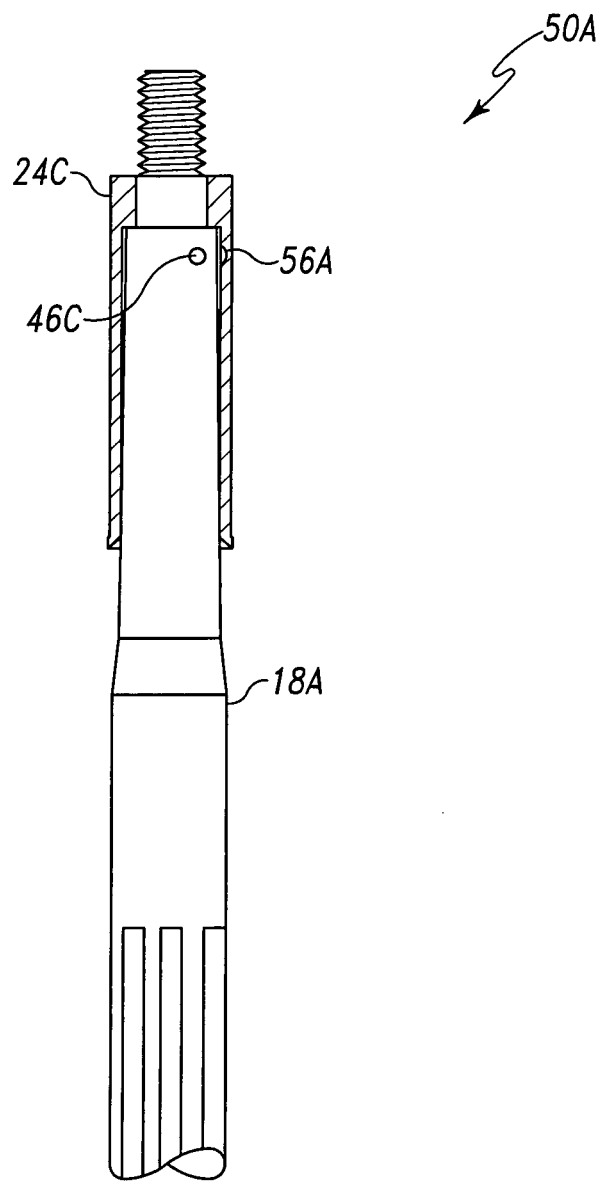
FIG. 4A is a plan view of a distal implant stem with an external protrusion for use with the sleeve of FIG. 3C installed on the stem, to form a distal implant sleeve assembly according to another embodiment of the present invention.
Figure 4B:
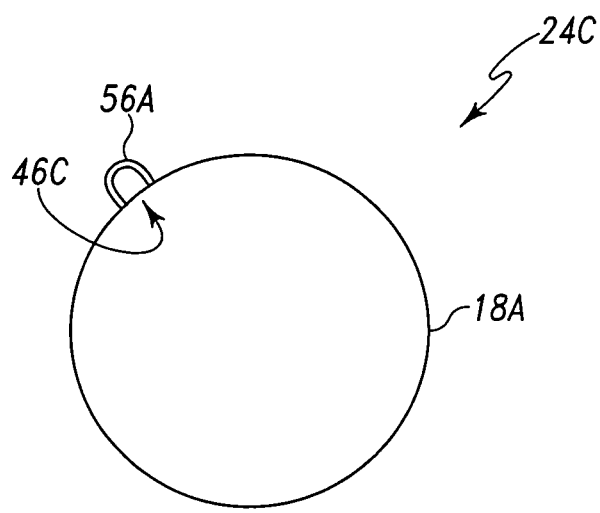
FIG. 4B is an end view of the distal implant sleeve assembly of FIG. 4A showing the protrusion on the periphery of the distal implant stem.

Referring now to FIGS. 4A and 4B, yet another embodiment of the present invention is shown as implant sleeve assembly 50A. The implant sleeve assembly 50A is similar to the implant sleeve assembly 50 of FIG. 4, except that the implant sleeve assembly 50A includes a stem 18A which has a stem/sleeve connection feature in the form of a protrusion 56A extending from the stem 18A. The protrusion 56A fits into the single indentation 46C formed in the sleeve 24C of FIGS. 3C and 3D.

Figure 4C:
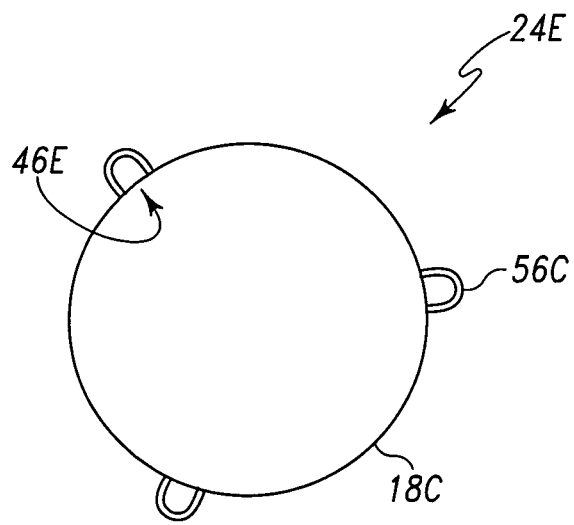
FIG. 4C is an end view of a distal implant stem with 3 spaced apart external protrusions for use with the sleeve of FIG. 3E installed on the stem, to form a distal implant sleeve assembly according to another embodiment of the present invention.

Referring now to FIG. 4C, yet another embodiment of the present invention is shown as implant/sleeve assembly 50C. The implant sleeve assembly 50C is similar to the implant/sleeve assembly 50A of FIGS. 4A and 4B except that stem 18 of the implant sleeve assembly 50C includes a plurality of spaced apart protrusions 56C extending from stem 18C. The protrusions 56C cooperate with a plurality of indents 46E formed on sleeve 24E.

Figure 4D:
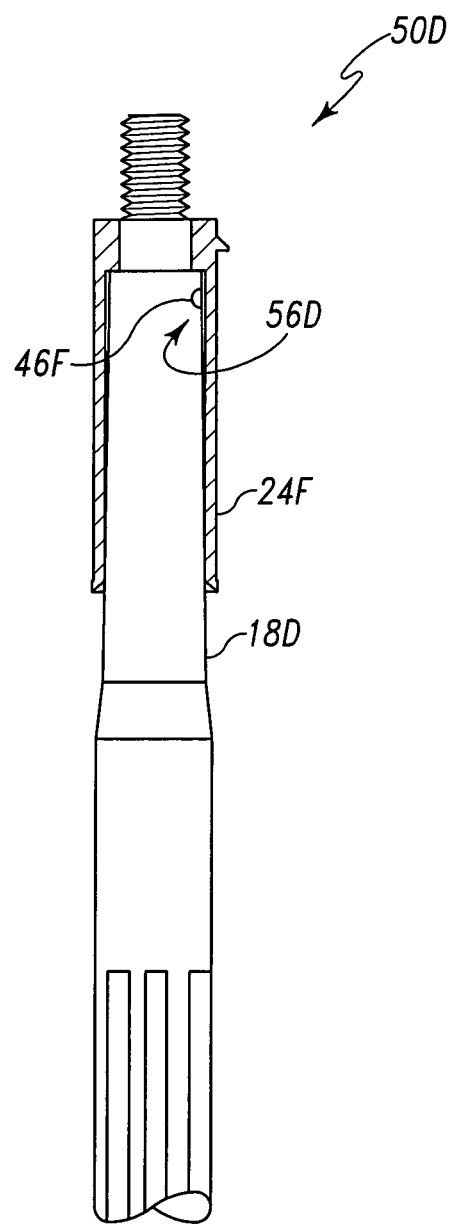
FIG. 4D is a plan view of a distal implant stem with an external indent for use with the sleeve of FIG. 3F installed on the stem, to form a distal implant sleeve assembly according to another embodiment of the present invention.
Figure 4E:
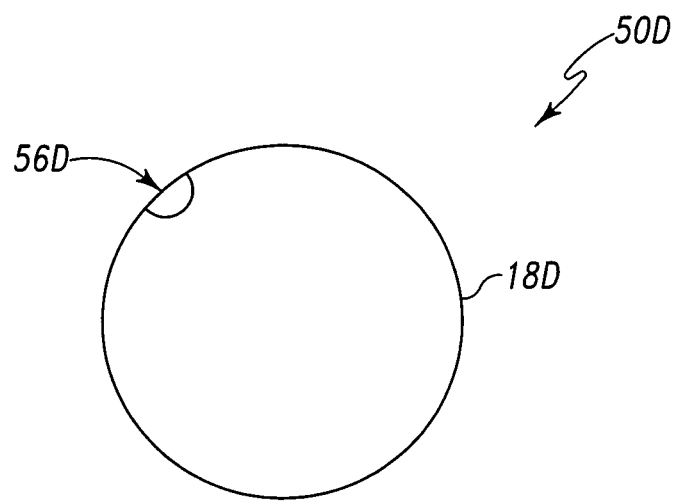
FIG. 4E is an end view of the distal implant sleeve assembly of FIG. 4D showing the protrusion on the external indent of the distal implant stem.

Referring now to FIGS. 4D and 4E, yet another embodiment of the present invention is shown as implant sleeve assembly 50D. The implant sleeve assembly 50D includes a solitary indent 56D formed on the stem 18D. The indent 56D on the stem 18D cooperates with a solitary protrusion 46F formed on sleeve 24F of FIGS. 3F and 3G.

Figure 4F:
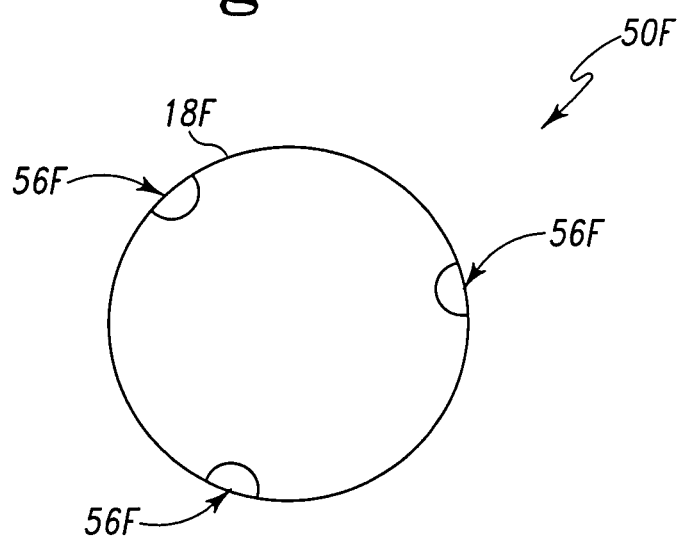
FIG. 4F is an end view of a distal implant stem with 3 spaced apart external indents for use with the sleeve of FIG. 3H installed on the stem, to form a distal implant sleeve assembly according to another embodiment of the present invention.

Referring now to FIG. 4F, yet another embodiment of the present invention is shown as implant sleeve assembly 50F. The implant sleeve assembly 50F is similar to the implant sleeve assembly 50D of FIGS. 4E and 4D. The implant sleeve assembly 50F includes a stem 18F which includes three spaced apart indentations 56F. The indentations 56F of the stem 18F cooperate with three spaced apart protrusions 46H formed on sleeve 24H of FIG. 3H.

Figure 4G:
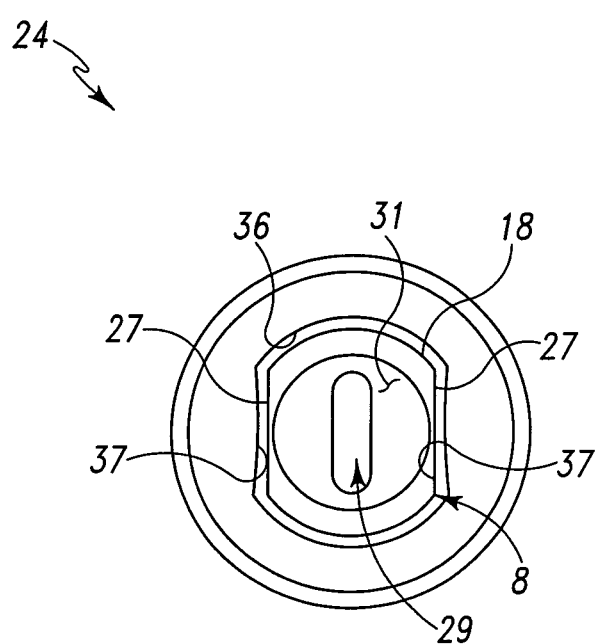
FIG. 4G is a top view of the implant/sleeve assembly of FIG. 4.

Referring now to FIG. 4G the sleeve 24 is shown in cooperation with the stem 18 of the distal reamer 8. The stem 18 of the distal reamer 8 includes opposed double flats 27 formed on stem 18. The proximal cylindrical portion 36 of the sleeve 24 includes opposed double flats 37 formed in the proximal cylindrical portion 36 of the sleeve 24. The opposed double flats 37 formed in the proximal cylindrical portion 36 of the sleeve 24 mate with the opposed double flats 27 formed on stem 18. The stem 18 of the distal reamer 8 also includes an elongated central recess 29 extending from end 31 of the stem 18 of the distal reamer 8.

Figure 4H:
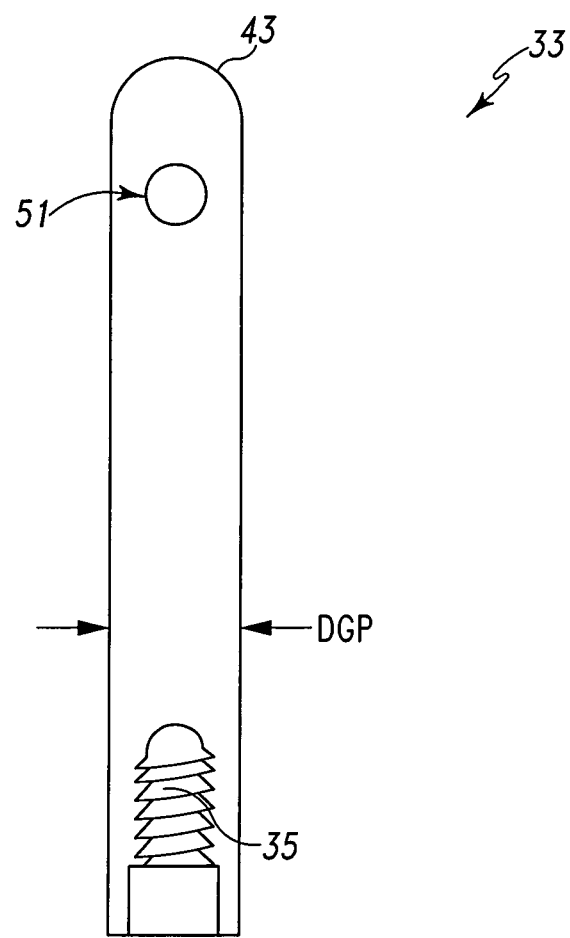
FIG. 4H is a plan view of a guide pin for use with the assembly of FIG. 4 to protect the sleeve of FIG. 3.
Figure 4:
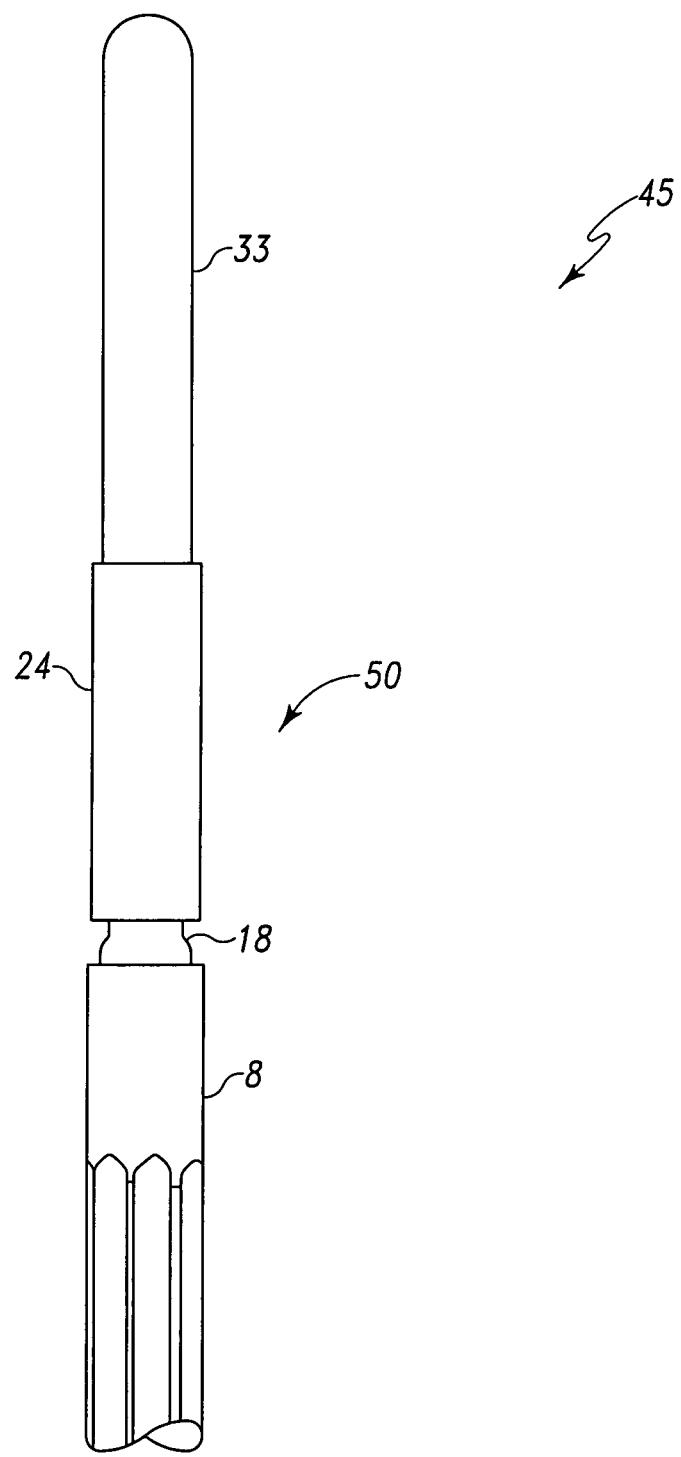

Referring now to FIG. 4H a guide pin 33 for use with the implant sleeve assembly 50 of FIG. 4 to protect the sleeve 18 of FIGS. 3N, 3P and 3Q. The guide pin 33 fits onto the external threads 23 on the stem 18 of distal reamer 8 of FIG. 1. The guide pin 33 includes internal threads 35 for mating with the external threads 23 on the stem 18 of distal reamer 8. The guide pin 33 may have any shape for fitting into the proximal reamer 58 of FIG. 5. For example the guide pin 33 may have a generally cylindrical shape define by diameter DGP. The guide pin 33 may have a rounded or bullet nose 43 to assist in guiding the reamer 58 onto the guide pin 33. The guide pin may include a through transverse opening 51 for use in extracting the guide pin 33.

Referring now to FIG. 4I the guide pin 33 of FIG. 4H is shown assembled onto the implant/sleeve assembly 50 of FIG. 4 to form an implant/sleeve/pin assembly 45. The proximal reamer 58 of FIG. 5 is guided onto the implant/sleeve/pin assembly 45.

Figure 5:
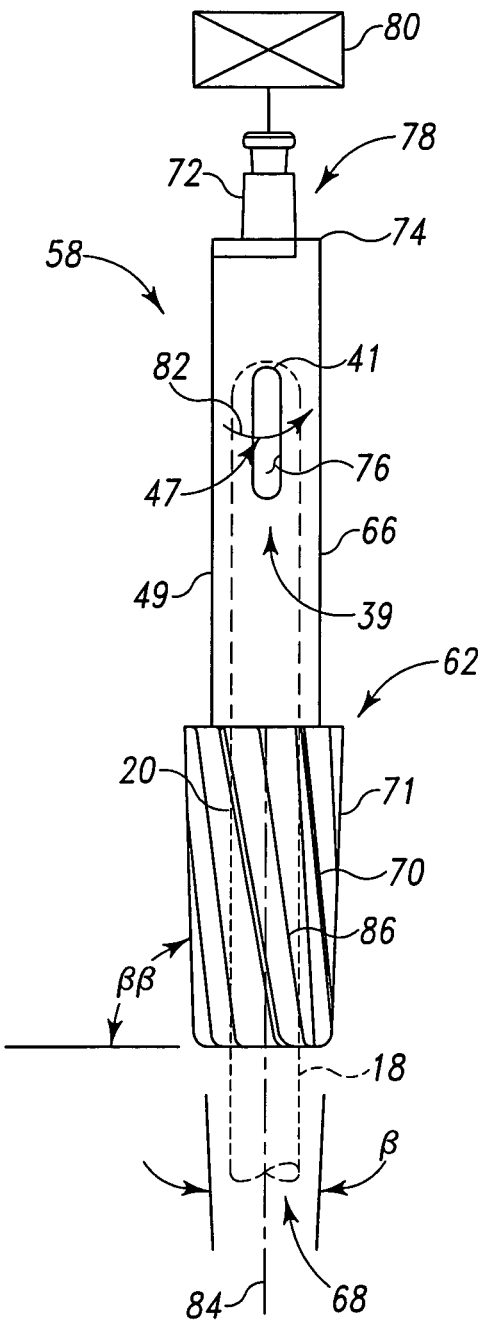
FIG. 5 is a plan view of a reamer for use with the implant/sleeve/pin assembly of FIG. 4I according to another embodiment of the present invention.

Referring now to FIG. 5, yet another embodiment of the present invention is shown as reamer 58. The reamer 58 is utilized for reaming a proximal portion 62 of the cavity 10 formed in the canal 4 of the femur 2. The reamer 58 is for use in implanting a joint prosthesis 62. The joint prosthesis 62 includes the distal stem portion 18. The reamer 58 includes a body 66 defining a distal cavity 68 formed in the body 66. The distal cavity 68 is adapted to receive at least a portion of the orthopedic implant component, for example, stem 18.

The reamer 58 also includes a plurality of cutting edges 70 extending outwardly from the body 66. The edges 70 are adapted for cooperation with bone, for example, the femur 2. The reamer 58 further includes a stem 72 extending from an end 74 of the body 66. The body 66 may have any suitable shape and may for example, be cylindrical, have a polygon cross-section, or have a periphery 76 that is tapered. The stem 72 may have any suitable shape and may include a connector 78 in the form of, for example, a standard commercially available connector, for example, a AO connector or an Hudson connector, capable of receiving a tool, for example, a driver 80 for rotating the reamer 58 in the direction of arrow 82. The reamer 58 includes cutting edges 70 that engage and remove bone.

The reamer 58 may have any suitable shape and may have any number of cutting edges 70. For example, there may be two, three, four, five, seven or more flutes. Preferably, the flutes are equally spaced and extend longitudinally along longitudinal center line 84 of the proximal reamer 58. The flutes 70 may run longitudinally with the longitudinal axis 84 or may as is shown in FIG. 5 be helical or form an angle, for example angle ββ with respect to the horizontal.

The distal cavity 68 formed in the proximal reamer 58 may have any suitable shape and may for example be cylindrical or have an external periphery 86 which defines a cone. The internal periphery 86 of the proximal reamer 58 defines the distal cavity 68 and, preferably, has a shape that mates with the proximal portion 20 of the stem 18.

As shown in FIG. 5, external periphery 71 of reamer 58 is defined by cutting edges 70 and may be tapered. The internal periphery 86 formed by the distal cavity 68 may also be tapered. It should be appreciated that other shapes of these components maybe within the scope of the invention. The reamer 58 includes a proximal internal cavity 39 for receiving the guide pin 33 of FIG. 4H. The proximal internal cavity 39 defines an end 41 of the internal cavity that provides a stop for cooperation with the bullet nose 43 of the guide pin 33. The reamer 58 may also include longitudinal slots 47 extending from the outer periphery 49 of the reamer to the proximal internal cavity 39 for viewing the insertion of the guide pin 33 into the reamer 58 and to ease cleaning of the reamer 58. The reamer 58 may have a solitary or multiple (for example 3 equally spaced apart) slots 47.

Figure 5A:
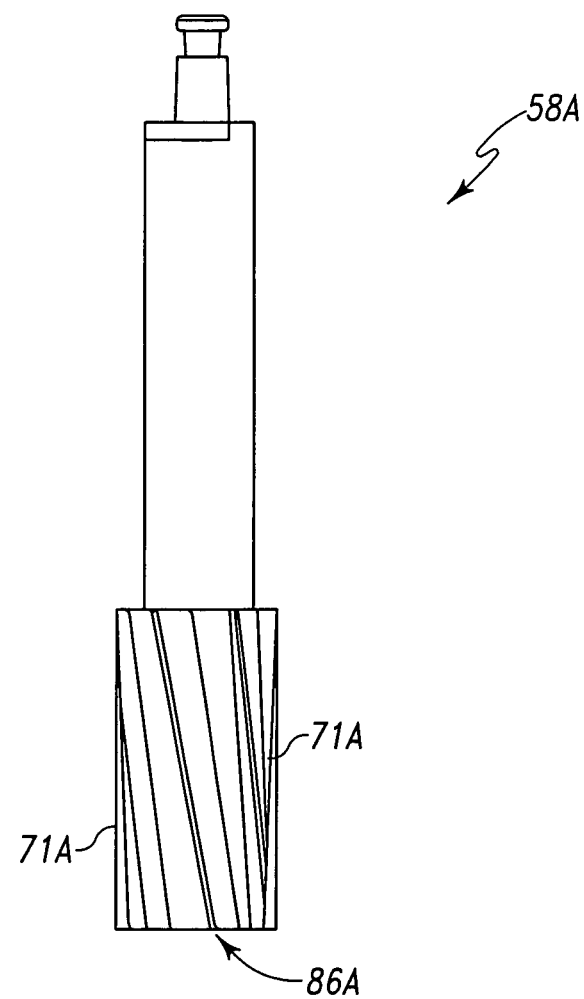
FIG. 5A is a plan view of a reamer for use with a distal stem component having a cylindrical outer periphery, the reamer having a cylindrical opening an a cylindrical periphery according to another embodiment of the present invention.

Referring now to FIG. 5A, another embodiment of the present invention is shown as proximal reamer 58A. Proximal reamer 58A is similar to the proximal reamer 58 of FIG. 5 except that the proximal reamer 58A includes cutting edges 70A that form an external periphery 71A that is cylindrical. Also, cavity 68A forms an internal periphery 86A which is, likewise, cylindrical.

Figure 5B:
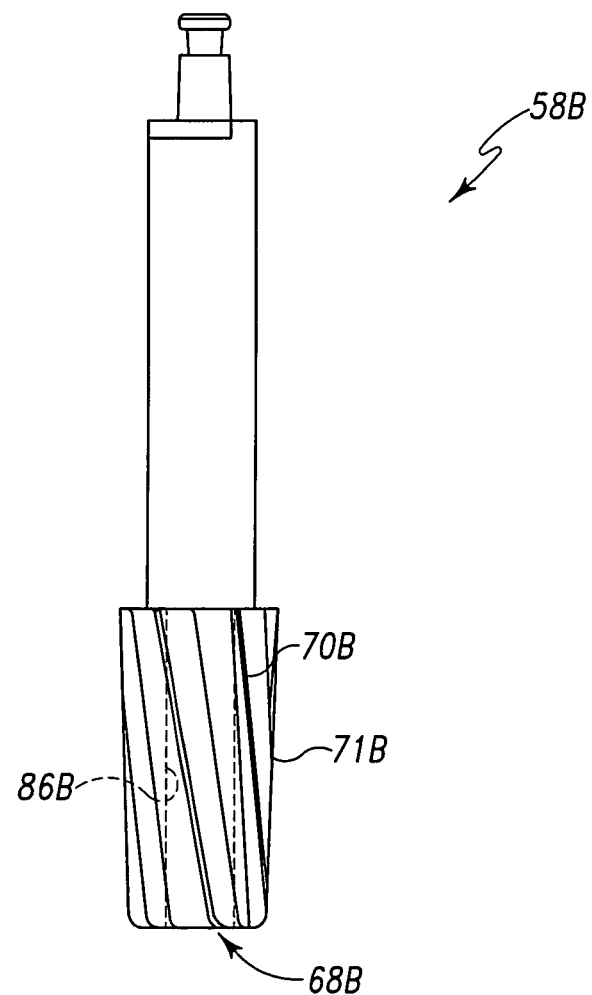
FIG. 5B is a plan view of a reamer for use with a distal stem component having a cylindrical outer periphery, the reamer having a cylindrical opening and a tapered periphery according to another embodiment of the present invention.

Referring now to FIG. 5B, yet another embodiment of the present invention is shown as reamer 58B. The reamer 58B is similar to the reamer 58 of FIG. 5 except that the reamer 58B includes a cavity 68B which forms an interior periphery 86B which is cylindrical. Cutting edges 70B form an external periphery 71B which is tapered or conical. The external periphery 71B is defined by included angle αα.

Figure 5C:
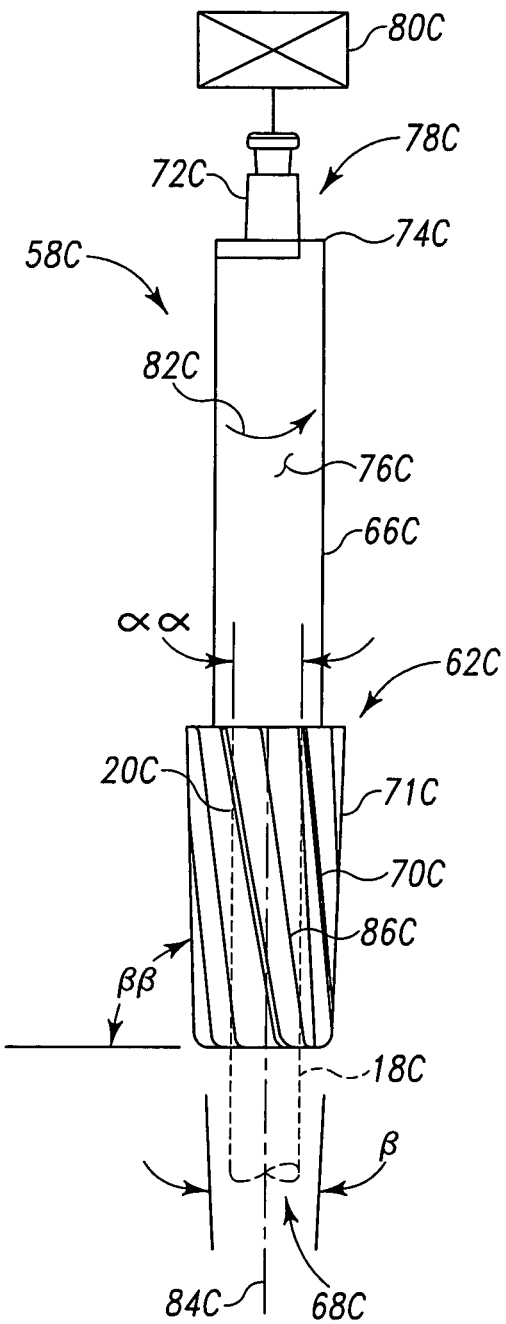
FIG. 5C is a plan view of a reamer for use with a distal stem component according to another embodiment of the present invention.

Referring now to FIG. 5C, yet another embodiment of the present invention is shown as reamer 58C. The reamer 58C is utilized for reaming a proximal portion 62C of the cavity 10 formed in the canal 4 of the femur 2. The reamer 58C is for use in implanting a joint prosthesis 62. The joint prosthesis 62 includes the distal stem portion 18. The reamer 58C includes a body 66C defining a cavity 68C formed in the body 66C. The cavity 68C is adapted to receive at least a portion of the orthopedic implant component, for example, stem 18.

The reamer 58C also includes a plurality of cutting edges 70C extending outwardly from the body 66C. The edges 70C are adapted for cooperation with bone, for example, the femur 2. The reamer 58C further includes a stem 72C extending from an end 74C of the body 66C. The body 66C may have any suitable shape and may for example, be cylindrical, have a polygon cross-section, or have a periphery 76C that is tapered. The stem 72C may have any suitable shape and may include a connector 78C in the form of, for example, a standard commercially available connector, for example, a AO connector or an Hudson connector, capable of receiving a tool, for example, a driver 80C for rotating the reamer 58C in the direction of arrow 82C. The reamer 58C includes cutting edges 70C that engage and remove bone.

The reamer 58C may have any suitable shape and may have any number of cutting edges 70C. For example, there may be two, three, four, five, seven or more flutes. Preferably, the flutes are equally spaced and extend longitudinally along longitudinal center line 84C of the proximal reamer 58C. The flutes 70C may run longitudinally with the longitudinal axis 84C or may as is shown in FIG. 5C be helical or form an angle, for example angle ββ with respect to the horizontal.

The cavity 68C formed in the proximal reamer 58C may have any suitable shape and may for example be cylindrical or have an external periphery 86C which defines a cone. The internal periphery 86C of the proximal reamer 58C defines the distal cavity 68 and, preferably, has a shape that mates with the proximal portion 20 of the stem 18.

As shown in FIG. 5C, external periphery 71C of reamer 58C is defined by cutting edges 70C and may be tapered. The internal periphery 86C formed by the cavity 68C may also be tapered. It should be appreciated that other shapes of these components maybe within the scope of the invention.

Figure 6:
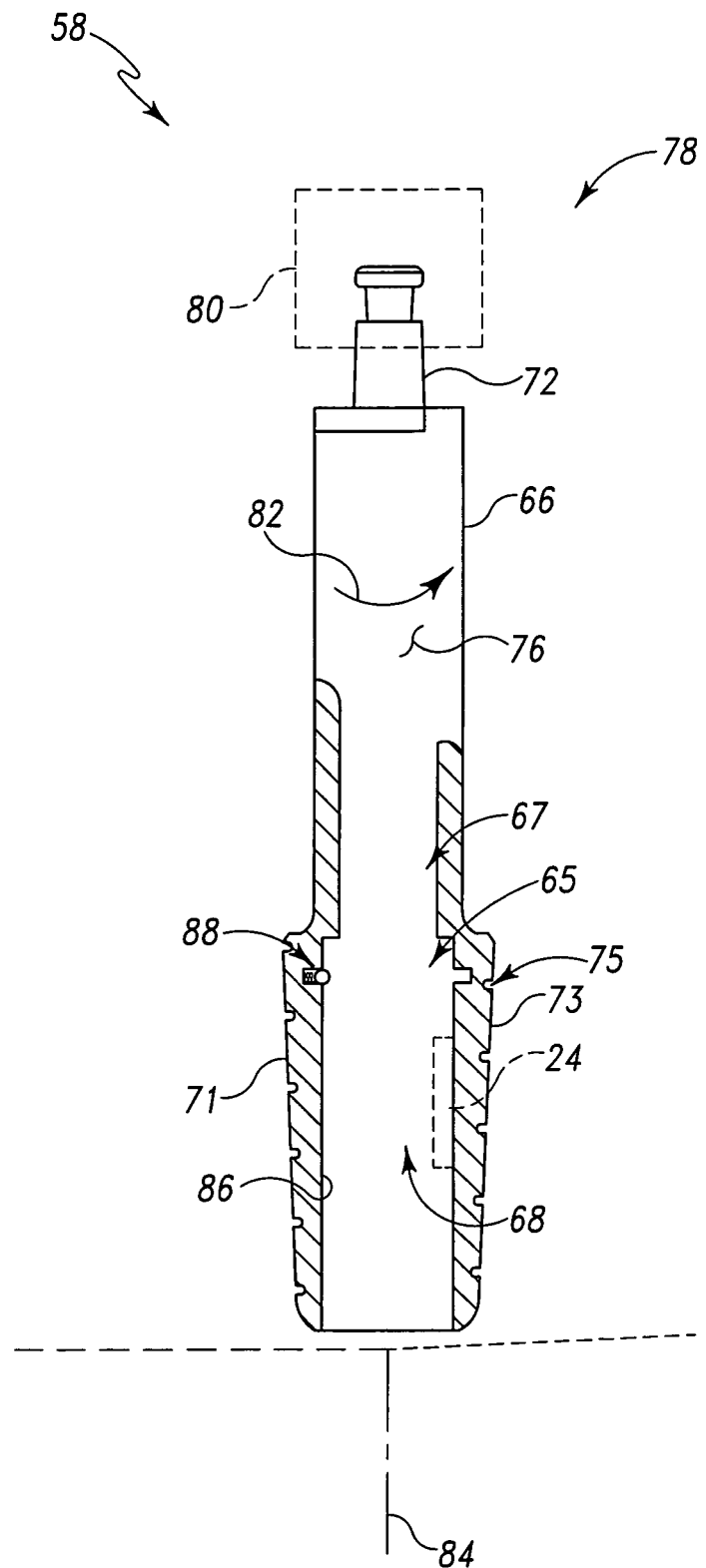
FIG. 6 is a plan view of the reamer of FIG. 5, partially in cross section.

Referring now to FIG. 6, the cutting edge 70 of the reamer 58 may have any suitable form. For example, the cutting edge 70 may include a plurality of spaced apart flutes 73. Each of the flutes 73 may as shown in FIG. 6 include a grouping of spaced apart reliefs 75. The reliefs may be positioned on each of the flutes 73 and may form circular rings or as shown in FIG. 6 be spirally positioned around the reamer external periphery 71.

The reamer 58 may include an attachment feature 88 for cooperation with the sleeve 24 such that the sleeve 24 is removed with the reamer 58 when the reamer has completed preparing the cavity for the proximal body. The attachment feature 88 may have any suitable size and shape to assist in having the sleeve 24 be removed with the reamer 58.

Figure 6A:
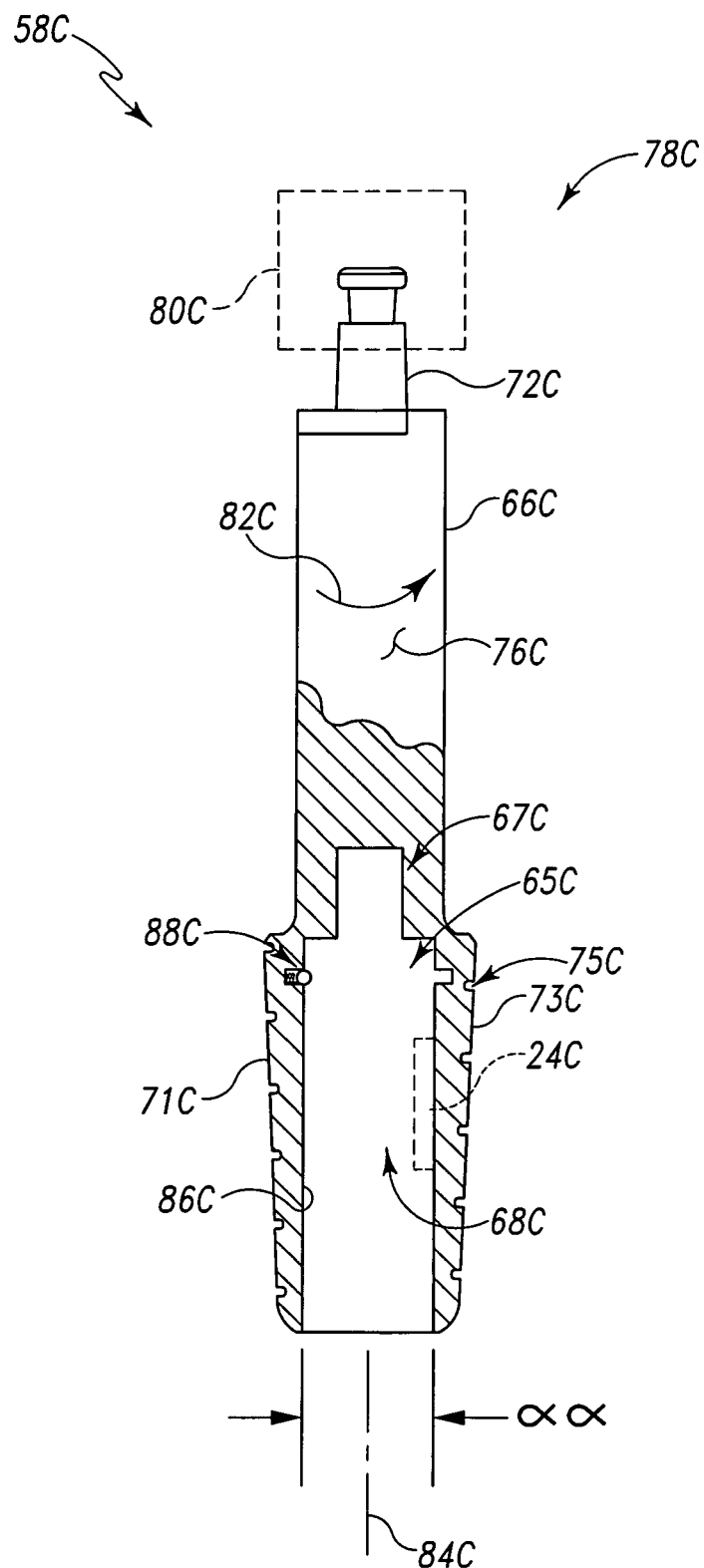
FIG. 6A is a plan view of the reamer of FIG. 5C, partially in cross section.

Referring now to FIG. 6A, the cutting edge 70C of the reamer 58C may have any suitable form. For example, the cutting edge 70C may include a plurality of spaced apart flutes 73C. Each of the flutes 73C may as shown in FIG. 6C include a grouping of spaced apart reliefs 75C. The reliefs may be positioned on each of the flutes 73C and may form circular rings or as shown in FIG. 6C be spirally positioned around the reamer external periphery 71C.

The reamer 58C may include an attachment feature 88C for cooperation with the sleeve 24X of FIG. 3 such that the sleeve 24X is removed with the reamer 58C when the reamer has completed preparing the cavity for the proximal body. The attachment feature 88C may have any suitable size and shape to assist in having the sleeve 24X be removed with the reamer 58C.

Figure 7:
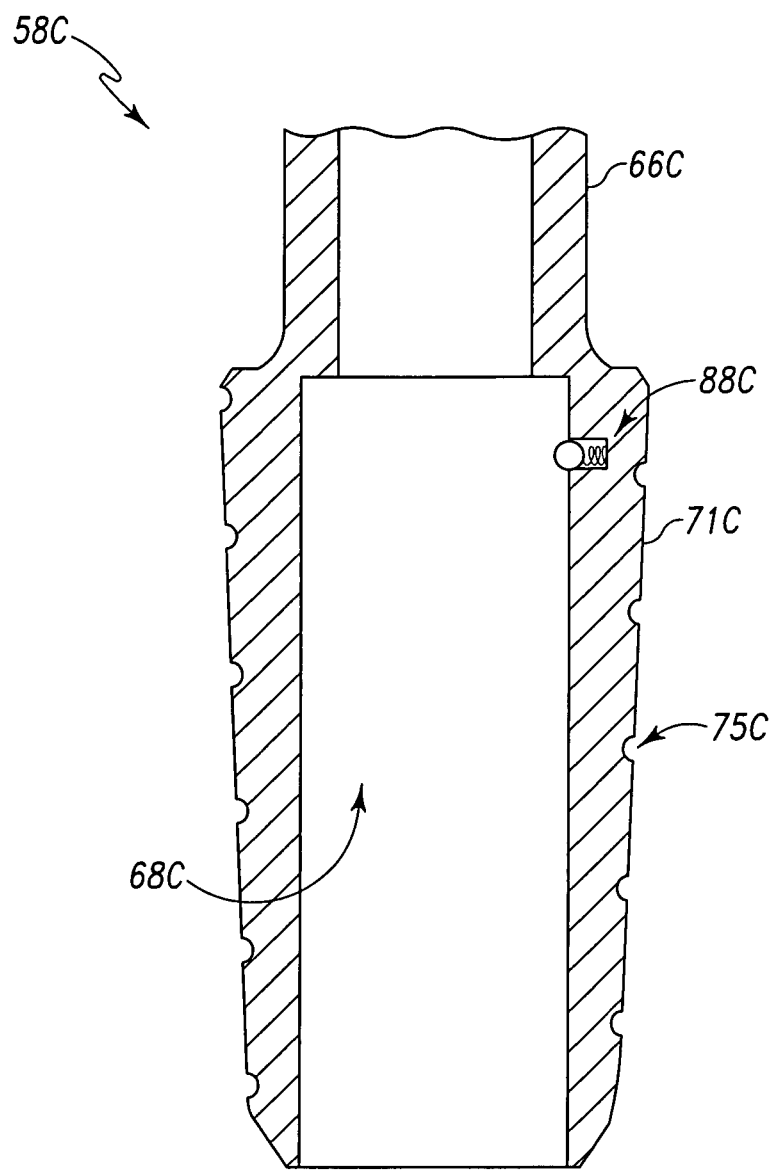
FIG. 7 is a plan view, partially in cross section, of the reamer of FIG. 5C shown in greater detail.

Referring now to FIG. 7, the attachment feature 88C is shown in greater detail. The attachment feature 88C may be in the form of a protrusion or as shown in FIG. 7 be in the form of a spring loaded detent.

Figure 7A:
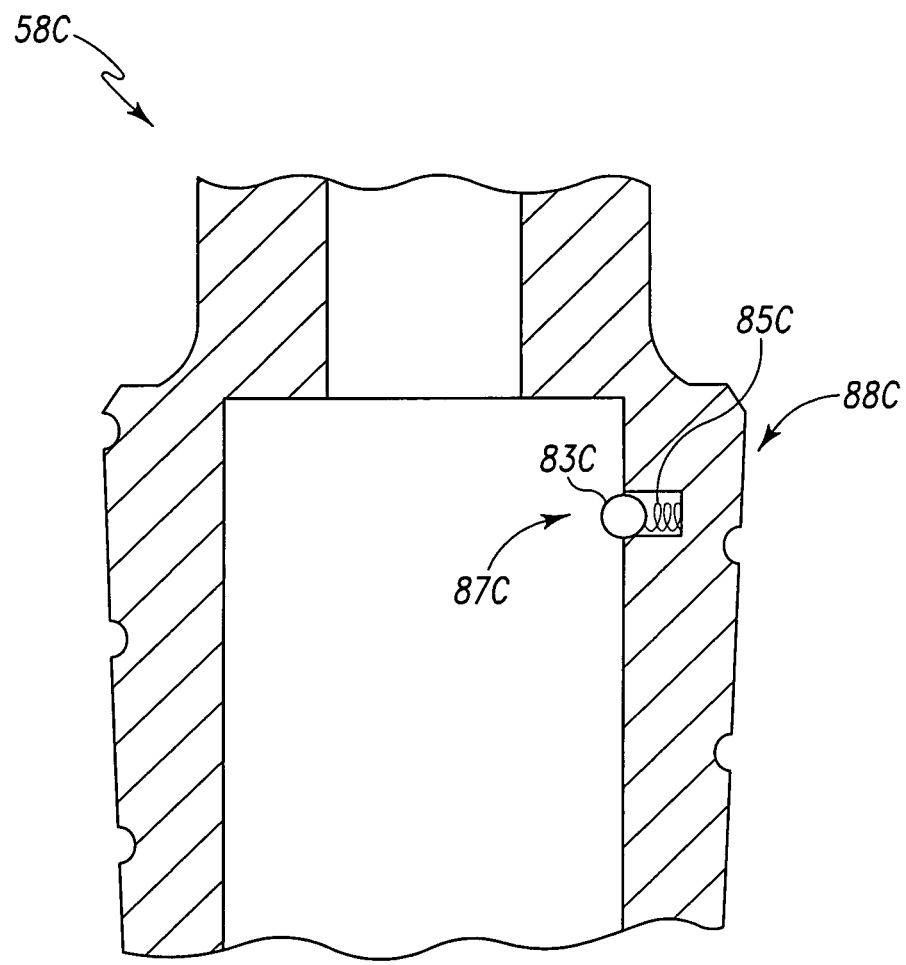
FIG. 7A is a partial plan view of FIG. 7A showing the spring loaded detent positioned in the bore of the reamer to mate with a groove on the external periphery of the sleeve in greater detail.

Referring now to FIG. 7A, the spring loaded detent 88C of the reamer 58C is shown in greater detail. The spring loaded detent 88C includes a ball 83C which is spring biased in the direction of the cavity 68C. The spring 85C and detent 88C are positioned in an opening 87C. The detent 88C receives the sleeve 24C by compressing the spring 85C and moving the ball 83C inwardly. The spring 85C then extends to engage the groove 48C in the sleeve 24C so that the sleeve 24C may be removed with the reamer 58C.

The ball 83C of the detent 88C cooperates with groove 48C of the sleeve 58C as shown in FIG. 3M. By providing the detent 88C to fit with a groove, for example groove 48M of FIG. 3M, the reamer 58C may rotate while the sleeve 24X is stationary or fixed to the distal stem 18.

Figure 7B:
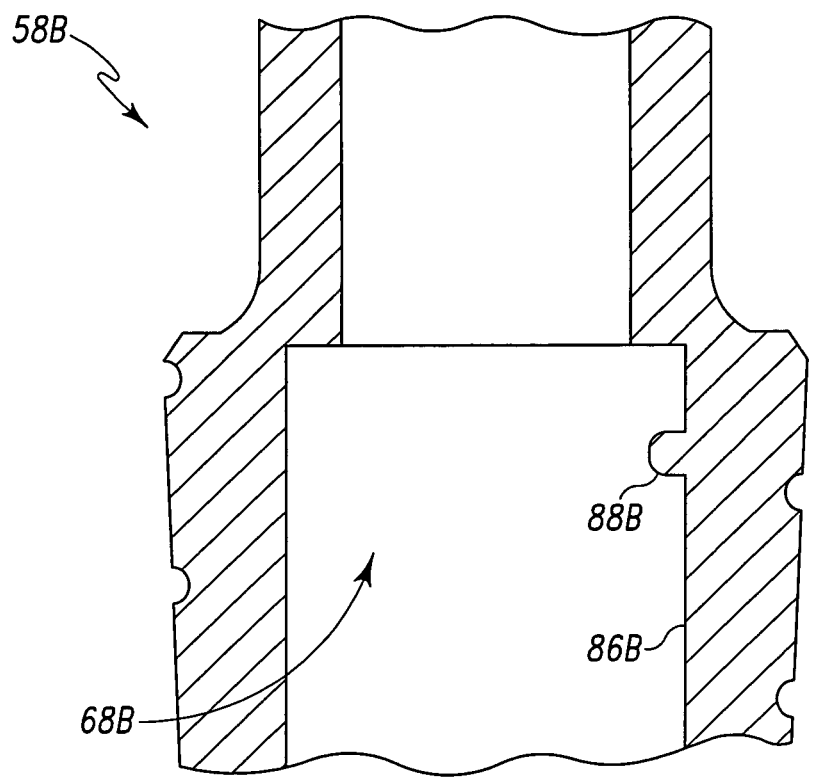
FIG. 7B is a partial plan view of a proximal reamer showing a protrusion positioned in the bore of the reamer to mate with a groove on the sleeve according to another embodiment of the present invention.
Figure 7C:
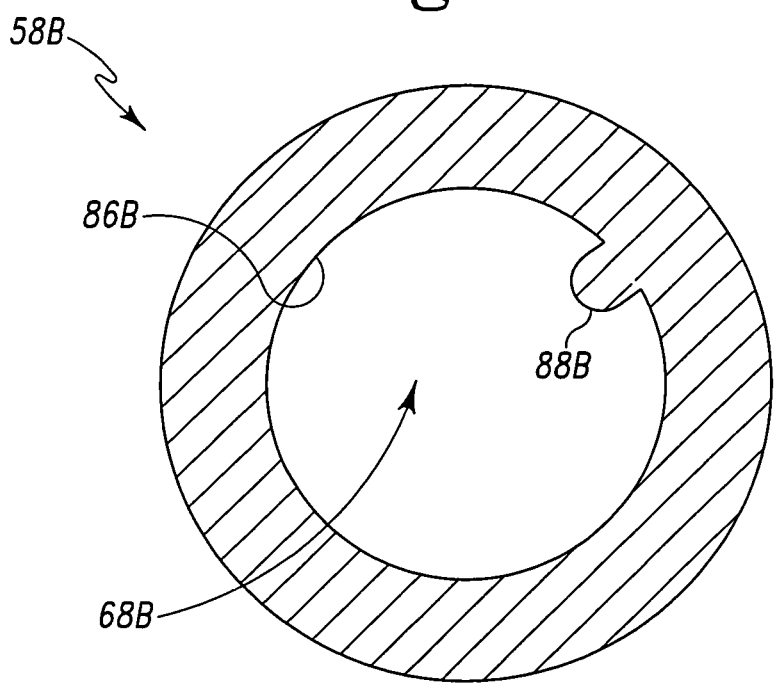
FIG. 7C is an end view of the proximal reamer of FIG. 7B showing the protrusion positioned in the bore of the reamer.

Referring now to FIGS. 7B and 7C, yet another embodiment of the present invention is shown as reamer 58B. Reamer 58B is similar to the reamer 58 of FIG. 7 except that the reamer 58B has a fixed solitary protrusion 88B which extends inwardly from internal periphery 86B of the cavity 68B of the reamer 58B. The protrusion 88B of reamer 58B cooperates with groove 48 of the sleeve 58, as shown in FIG. 3M.

Figure 7D:
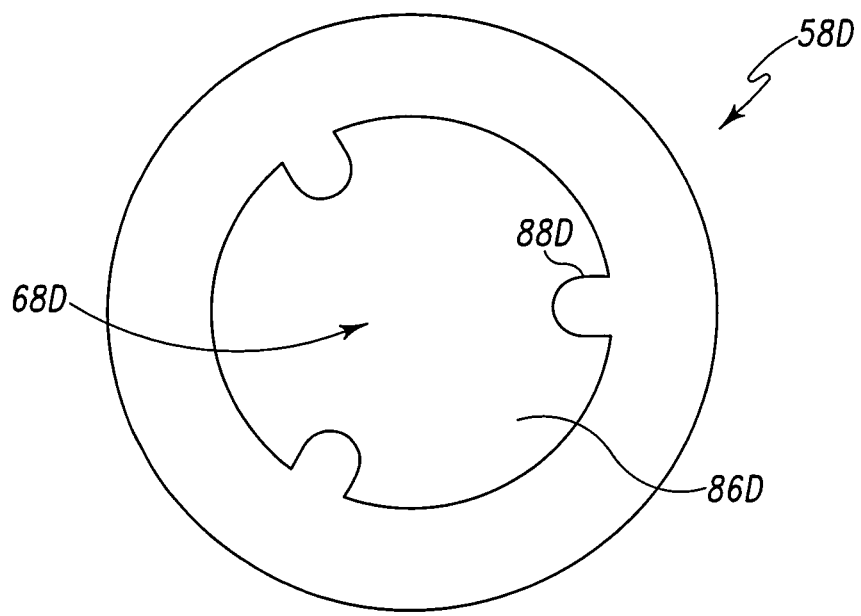
FIG. 7D is an end view of a proximal reamer of FIG. 7B showing 3 spaced apart protrusions positioned in the bore of the reamer according to another embodiment of the present invention.

According to the present invention and referring now to FIG. 7D, yet another embodiment of the present invention is shown as reamer 58D. The reamer 58D is similar to the reamer 58B of FIGS. 7B and 7C except that the reamer 58D includes three spaced apart protrusions 86D extending inwardly from internal periphery 86D of the cavity 68D of the reamer 58D. The protrusion 88D of reamer 58D cooperates with groove 48 of the sleeve 58, as shown in FIG. 3M.

The protrusion 88B of FIGS. 7B and 7C as well the protrusions 88D of the reamer 58D of FIG. 7D cooperate with a sleeve having a groove, for example sleeve 24 having groove 48, as shown in FIG. 3M. The protrusions and the groove cooperate such that the proximal reamer 58 may rotate while the stem 18 and the sleeve 24 are stationary.

Figure 7E:
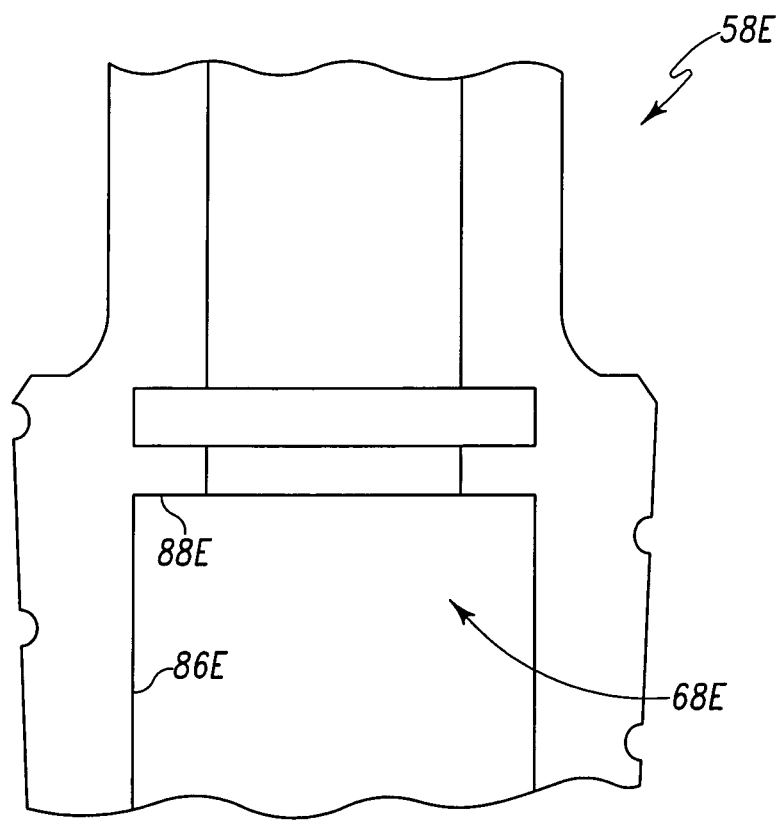
FIG. 7E is a partial plan view of a proximal reamer showing a ring positioned in the bore of the reamer to mate with a groove on the sleeve according to another embodiment of the present invention

Referring now to FIG. 7E, yet another embodiment of the present invention is shown as proximal reamer 58E. The proximal reamer 58E is similar to the reamer 58D of FIG. 7D except that a continuous rib 88E extends inwardly from internal periphery 86E of cavity 68E. The rib 88E cooperates with groove 48 formed in sleeve 24 as shown in FIG. 3M.

Figure 7F:
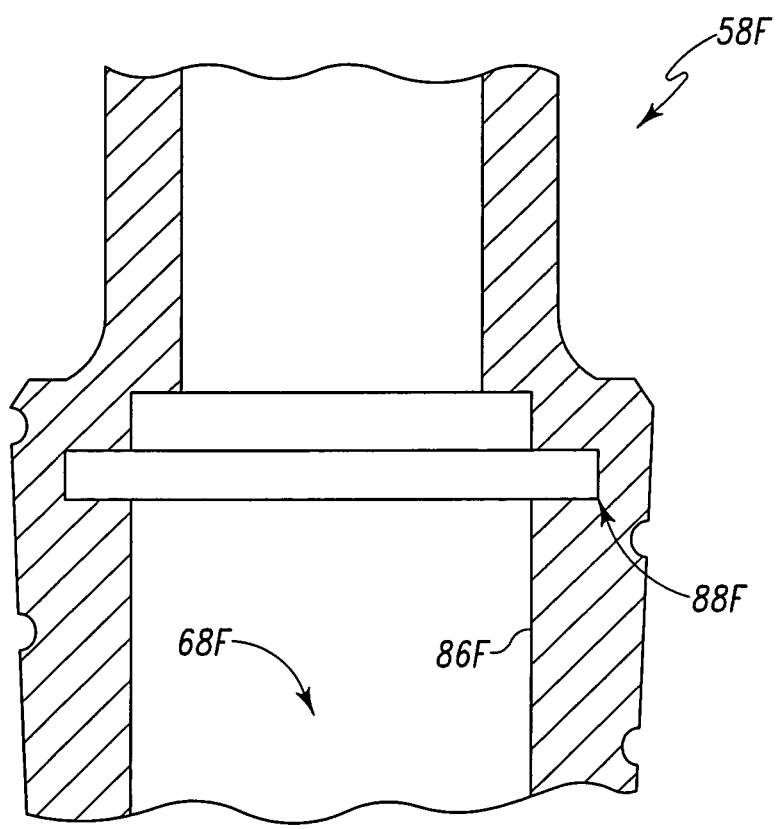
FIG. 7F is a partial plan view of a proximal reamer showing a groove positioned in the bore of the reamer to mate with a protrusion on the sleeve according to another embodiment of the present invention.

Referring now to FIG. 7F, yet another embodiment of the present invention is shown as reamer 58F. The reamer 58F is similar to the reamer 58E as shown in FIG. 7E except that the reamer 58F includes a circumferential interior groove 88F extending outwardly from internal periphery 86F formed in cavity 68F of the reamer 58F. The groove 88F cooperates with, for example, the single protrusion 24A of FIG. 3K or the rib 48K formed in sleeve 24K of FIG. 3K.

Figure 7G:
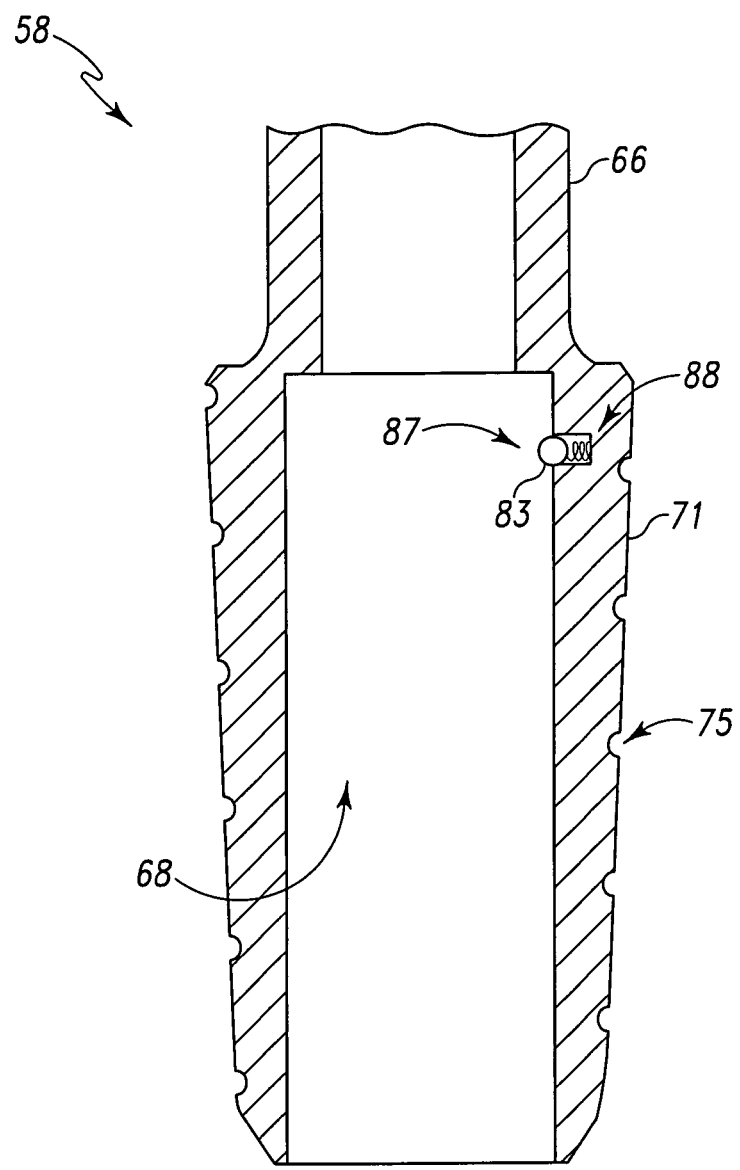
FIG. 7G is a plan view, partially in cross section, of the reamer of FIG. 5 shown in greater detail.

Referring now to FIG. 7G, the attachment feature 88 is shown in greater detail. The attachment feature 88 may be in the form of a protrusion or as shown in FIG. 7 be in the form of a spring loaded detent.

The spring loaded detent 88 includes a ball 83 which is spring biased in the direction of the distal cavity 68. The spring 85 and detent 88 are positioned in an opening 87. The detent 88 receives the sleeve 24 by compressing the spring 85 and moving the ball 83 inwardly. The spring 85 then extends to engage the groove 48 in the sleeve 24 so that the sleeve 24 may be removed with the reamer 58.

The ball 83 of the detent 88 cooperates with groove 48 of the sleeve 58 as shown in FIG. 3N. By providing the detent 88 to fit with a groove, for example groove 48 of FIG. 3N, the reamer 58 may rotate while the sleeve 24 is stationary or fixed to the distal stem 18.

Figure 8:
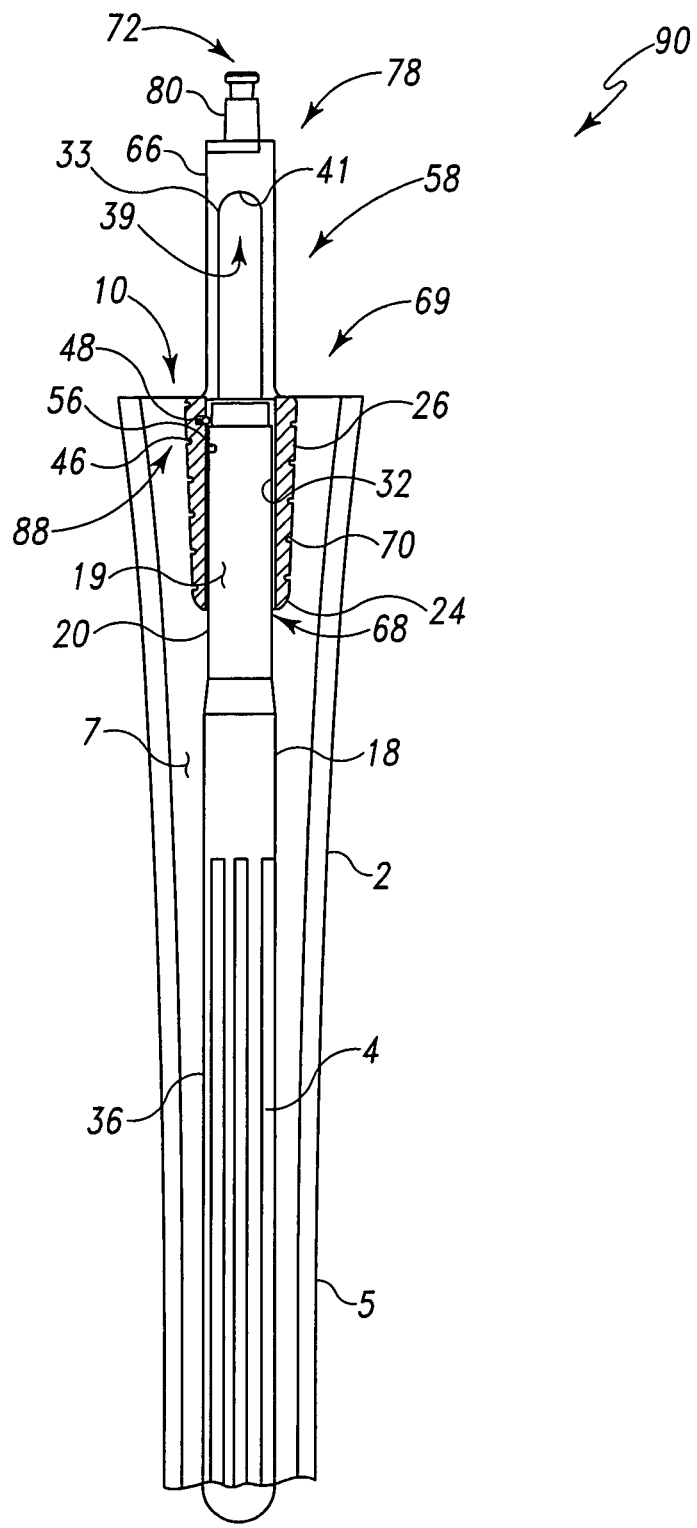
FIG. 8 is a plan view partially in cross section of the reamer of FIG. 5 in position on the distal implant/sleeve assembly of FIG. 4.

Referring now to FIG. 8 and according to present invention, reamer assembly 90 is shown. The sleeve 24 and the guide pin 33 are positioned in the proximal internal cavity 39 formed in the proximal reamer 58. The orthopedic implant stem 18 is positioned in the distal cavity 68 of the reamer 58 and the external periphery 19 of the proximal portion 20 of the stem 18 mates with the inner periphery 32 of the sleeve 24. The sleeve outer periphery 26 is rotatably engaged with internal periphery 86 of the reamer 58. The securing feature 48 of the sleeve 24 engages with the attachment feature 88 of the reamer 58. Similarly, the securing feature 56 of the stem 18 connects with the locking feature 46 of the sleeve 24.

Figure 9:
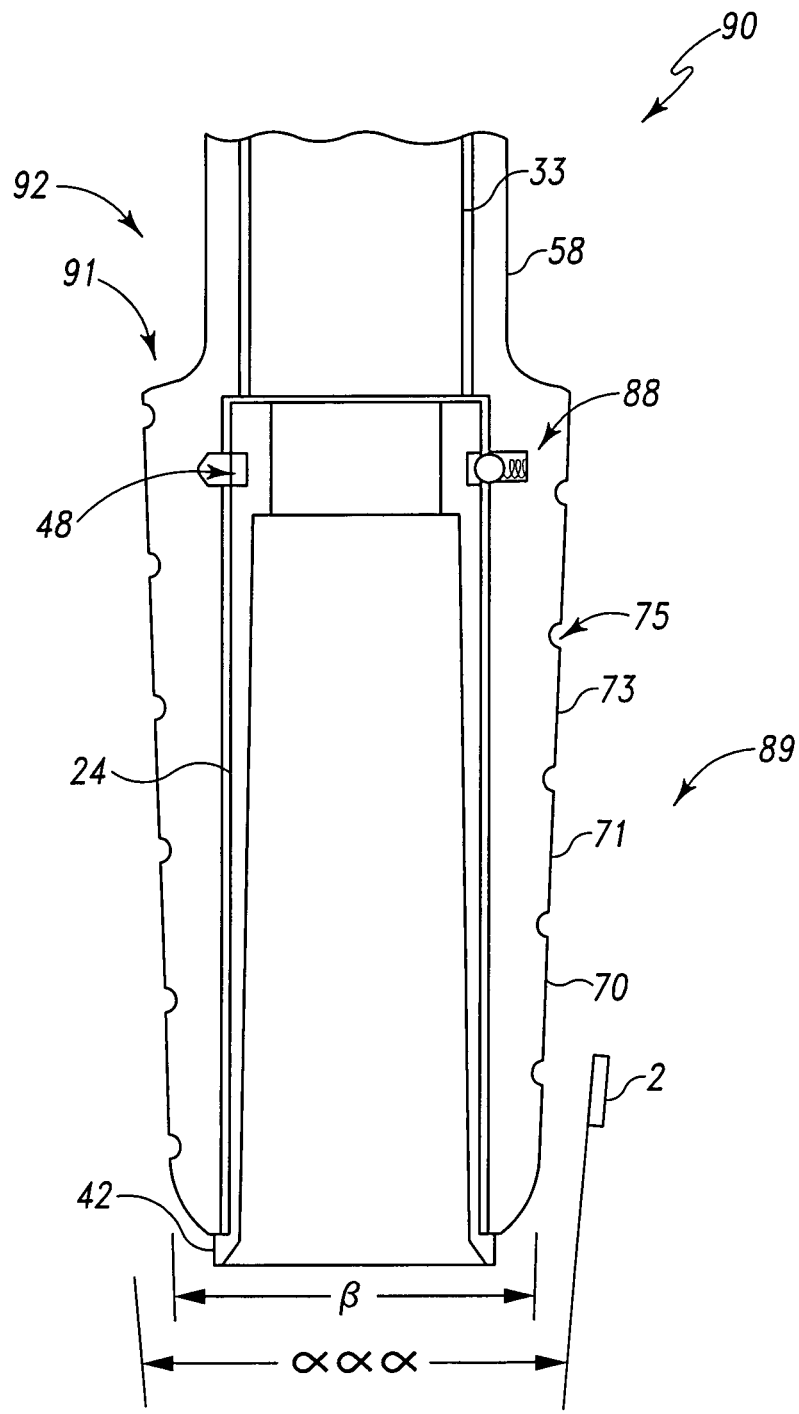
FIG. 9 is a partial plan view, partially in cross section, of the reamer of FIG. 5 with the sleeve of FIG. 3 in position on the reamer of FIG. 5 to form a reamer/sleeve assembly according to another embodiment of the present invention.

Referring now to FIG. 9, yet another embodiment of the present invention is shown as reamer sleeve assembly 92. The reamer sleeve assembly 92 includes the reamer 58 as well as the sleeve 24. As shown in FIG. 9, the reamer sleeve assembly includes a detent 88 formed on the reamer 58 which cooperates with groove 48 formed in the sleeve 24. The outer periphery 71 defined by the cutting edge 70 of the reamer 58 is utilized to remove bone from proximal portion 89 of the femur 2. Cutting edges 70 of the reamer 58 prepare cavity 91 in the proximal portion 89 of the femur 2. The proximal cavity 91 is defined by angle ααα which is generally similar to the angle β defined by the external periphery 71 of the reamer 58.

Referring now to FIG. 9, it should be appreciated that the lip 42 of the sleeve 24 cooperates with the groove 48 formed in the sleeve 24 and the D-tent 88 to securably position the sleeve 24 in the reamer 58.

Figure 10:
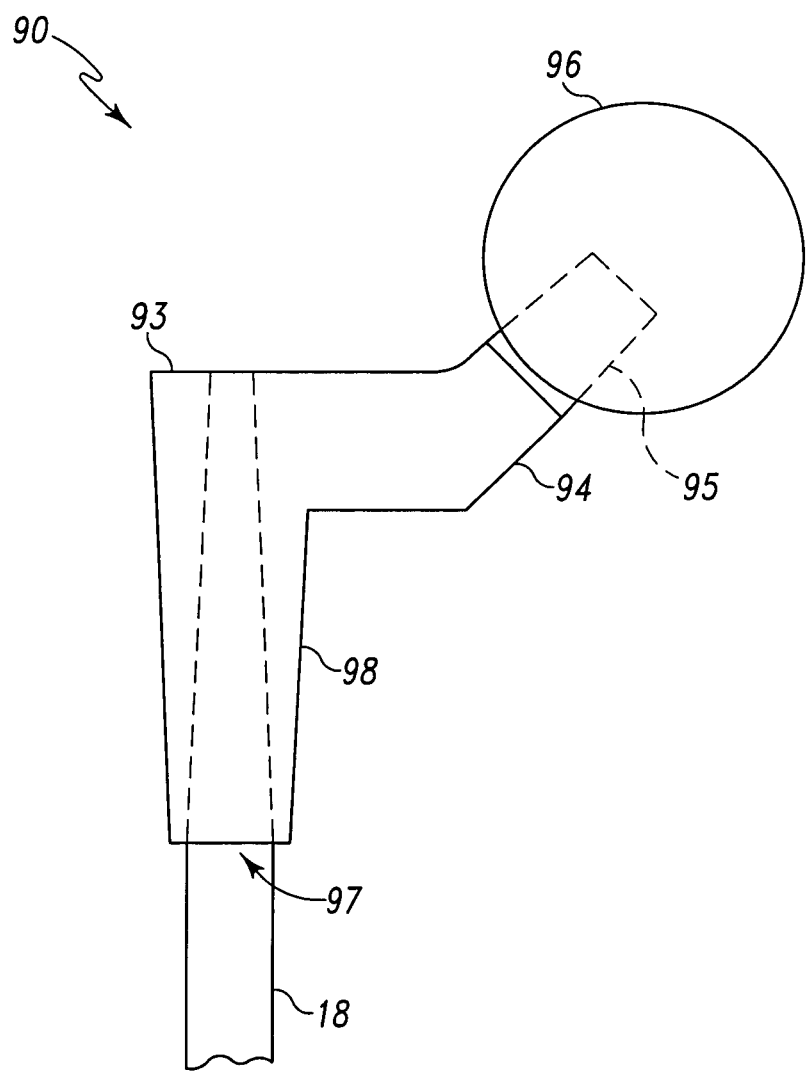
FIG. 10 is a proximal body implant for use with the distal stem implant of FIG. 2.

Referring now to FIG. 10, an orthopedic implant proximal component 90 is shown for use with the stem 18. The orthopedic implant proximal component 90 includes a body 93 for receiving head 96 of the prosthesis. The body 93 defines a longitudinal opening 97 for receiving the stem 18. The body 93 further defines an external portion 98 which is sized to fit within the opening 91 prepared in the proximal portion 89 of the femur 2 by the reamer 58 (See FIG. 9).

Figure 11:
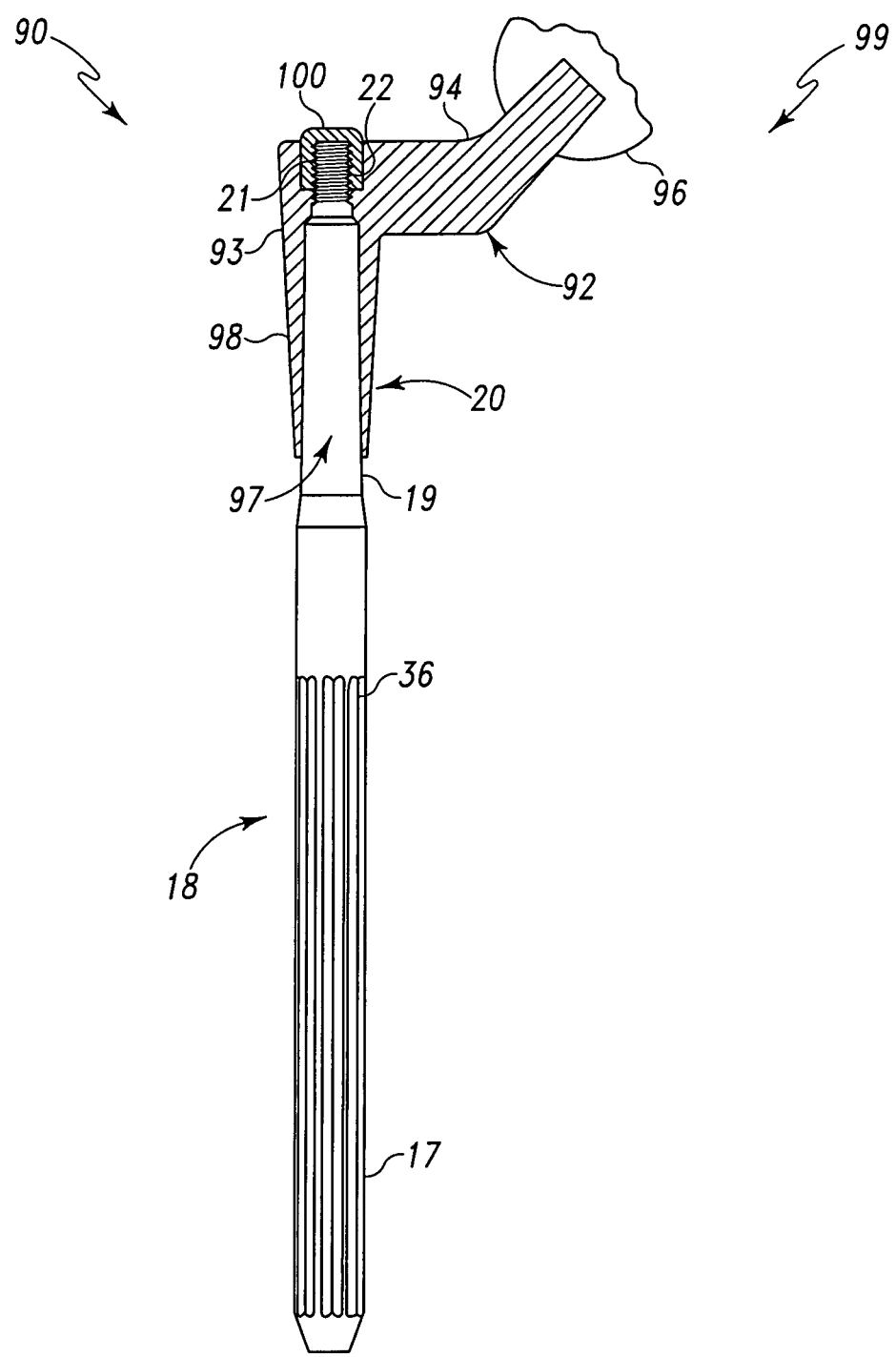
FIG. 11 is a long bone implant assembly including the proximal body implant of FIG. 10 in position on the long bone distal stem implant of FIG. 2.

Referring now to FIG. 11, a hip stem assembly 99 to be used with the reamer and reamer assembly of the present invention is shown. The hip stem assembly 99 includes distal implant stem 18 to which proximal body 93 is fixedly secured. The tapered portion 20 of the stem 18 is fitted into longitudinal opening 97 formed in body 93 of the proximal component 92. The tapered portion 20 of the stem 18 may include external threads 21 formed on threaded portion 22 of the stem 18. A fastener in the form of a nut 100 may be used to assure the complete seating of the tapered portion 20 of the stem 18 into the longitudinal opening 97. The nut 100 may be left on the orthopedic stem assembly 99 or may be removed once the stem 18 is securely fitted to the proximal component 92.

Figure 12:
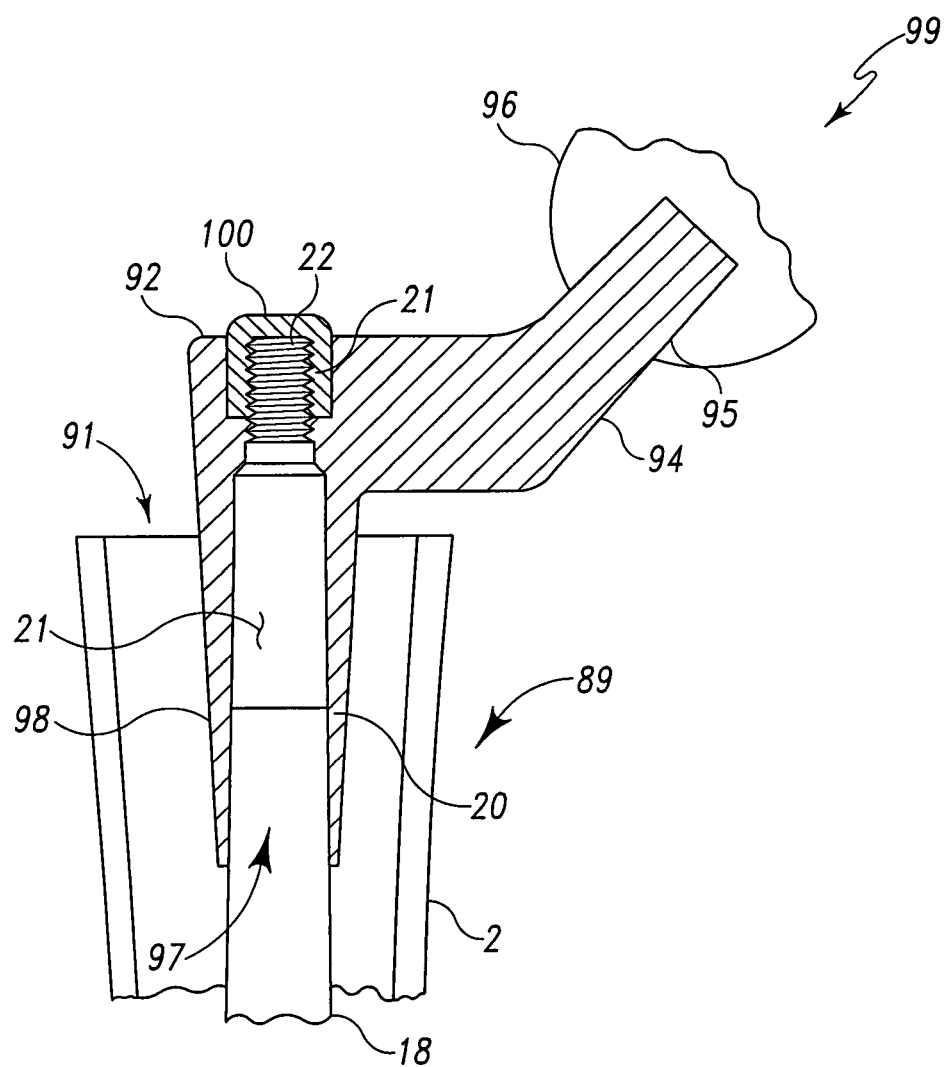
FIG. 12 is an enlarged partial plan view of the long bone implant assembly of FIG. 11 showing the tapered connection in greater detail.

Referring now to FIG. 12, the proximal component 92 is shown in greater detail. As shown in FIG. 12, the proximal portion 20 of the distal component 18 is shown fitted into longitudinal opening 97 of the proximal component 92. The threads 21 of the threaded portion 22 of the stem 18 engage the nut 100 and draw the stem into engagement with the proximal component 92. External periphery 98 of the proximal component 92 is fitted into cavity 91 formed by the proximal reamer 58. The neck 94 supports an externally tapered periphery 95 to which head 96 in the form of a spherical ball is securely fitted.

Figure 13:
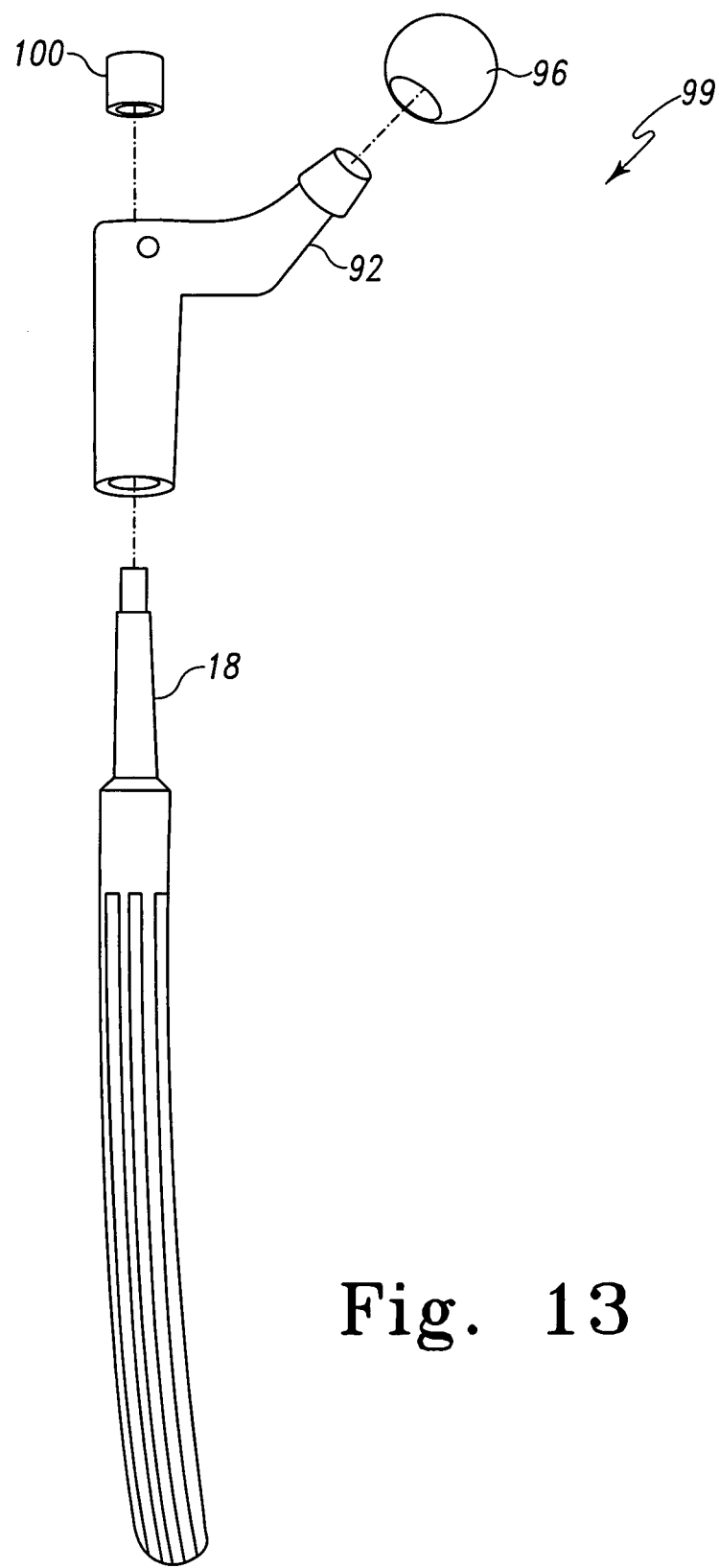
FIG. 13 is an exploded view of the long bone implant assembly of FIG. 11 including a head.

Referring now to FIG. 13, the components of the stem assembly 99 are shown in an exploded view. The stem 18, the proximal component 92, the head 96, and the nut 100 are shown in their respective position prior to assembly. As shown in FIG. 13, the stem 18 has an arcuate shape. The present invention is particularly well suited for use with orthopedic implants with a curved or bent stem. It should be appreciated however that the current invention may be used with straight or cylindrical or linear stems as well. It should be appreciated that when using an implant with a curved or arcuate stem, a reamer can not be provided for preparing simultaneously the distal cavity for the distal reamer and a closely fitting reamed portion for the proximal body as these two components do not have a common center line and thus can not be reamed simultaneously.

Figure 14:
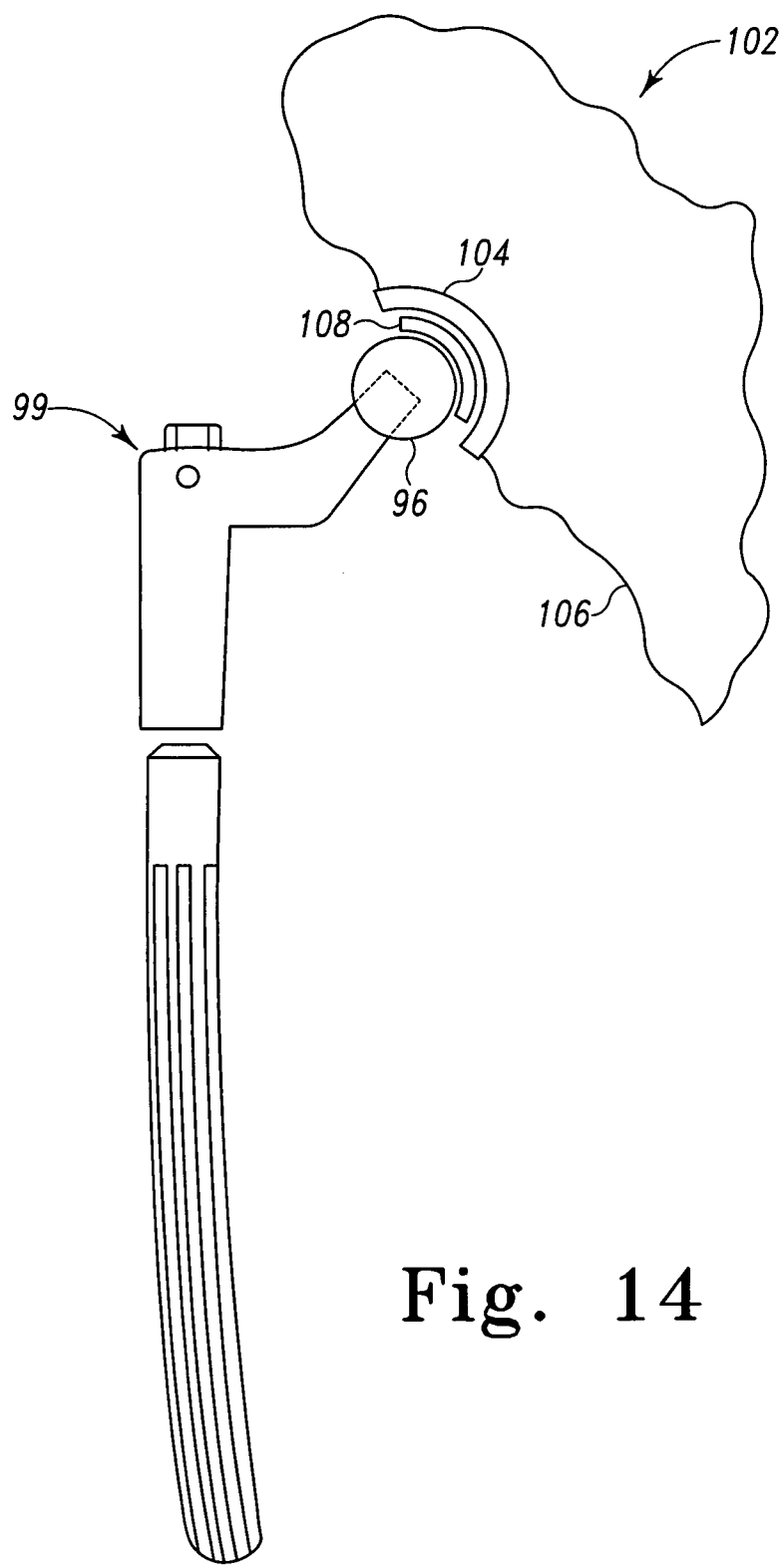
FIG. 14 is an assembled view of the long bone implant assembly of FIG. 13; in position in the body.

Referring now to FIG. 14, orthopedic implant assembly in the form of a hip prosthesis 102 is shown. The hip prosthesis 102 includes the stem assembly 99 as well as head 96. A shell or cup 104 may be secured onto acetabulum 106. The cup or shell 104 may mate directly with the head 96 or a liner or bearing 108 may be positioned between the cup 104 and the head 96. The orthopedic implant 102 may be made of any suitable material. The stem 99 may be made of any suitable durable material that is compatible with the human anatomy and may for example be made of a metal. If made of a metal, the orthopedic implant components may be made of, for example, cobalt chromium alloy, stainless steel alloy, or a titanium alloy. It should be appreciated that the liner or bearing 108 may be made of a metal or may be made of a plastic, for example, polyethylene.

Figure 15:
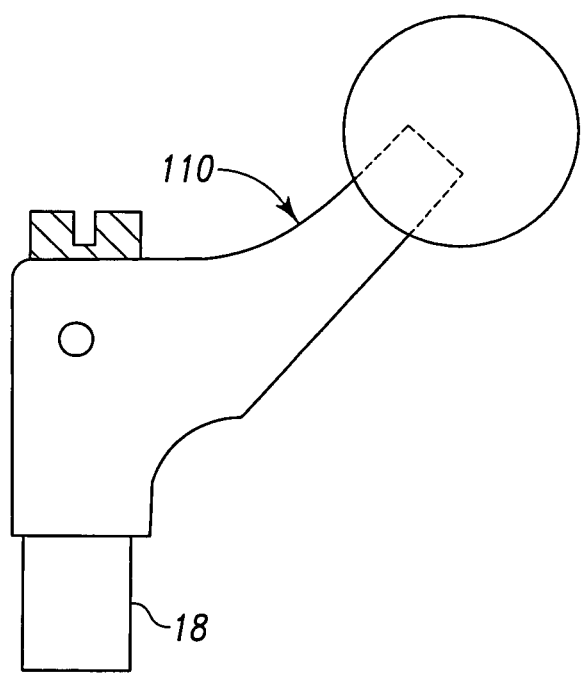
FIG. 15 is a proximal trial component for use with the long bone distal stem implant of FIG. 2.

Referring now to FIG. 15, a trial neck 110 is shown for use with the distal implant stem 18. The trial neck 110 substitutes for the proximal component 92 and may be utilized to provide a trial reduction to assure that the proper proximal component is used. A proximal implant similar to the trial neck 110 will be substituted once the trial reduction has been performed and the proximal trial neck 110 is found to be suitable, thus making the corresponding proximal component suitable for the patient.

Figure 16:
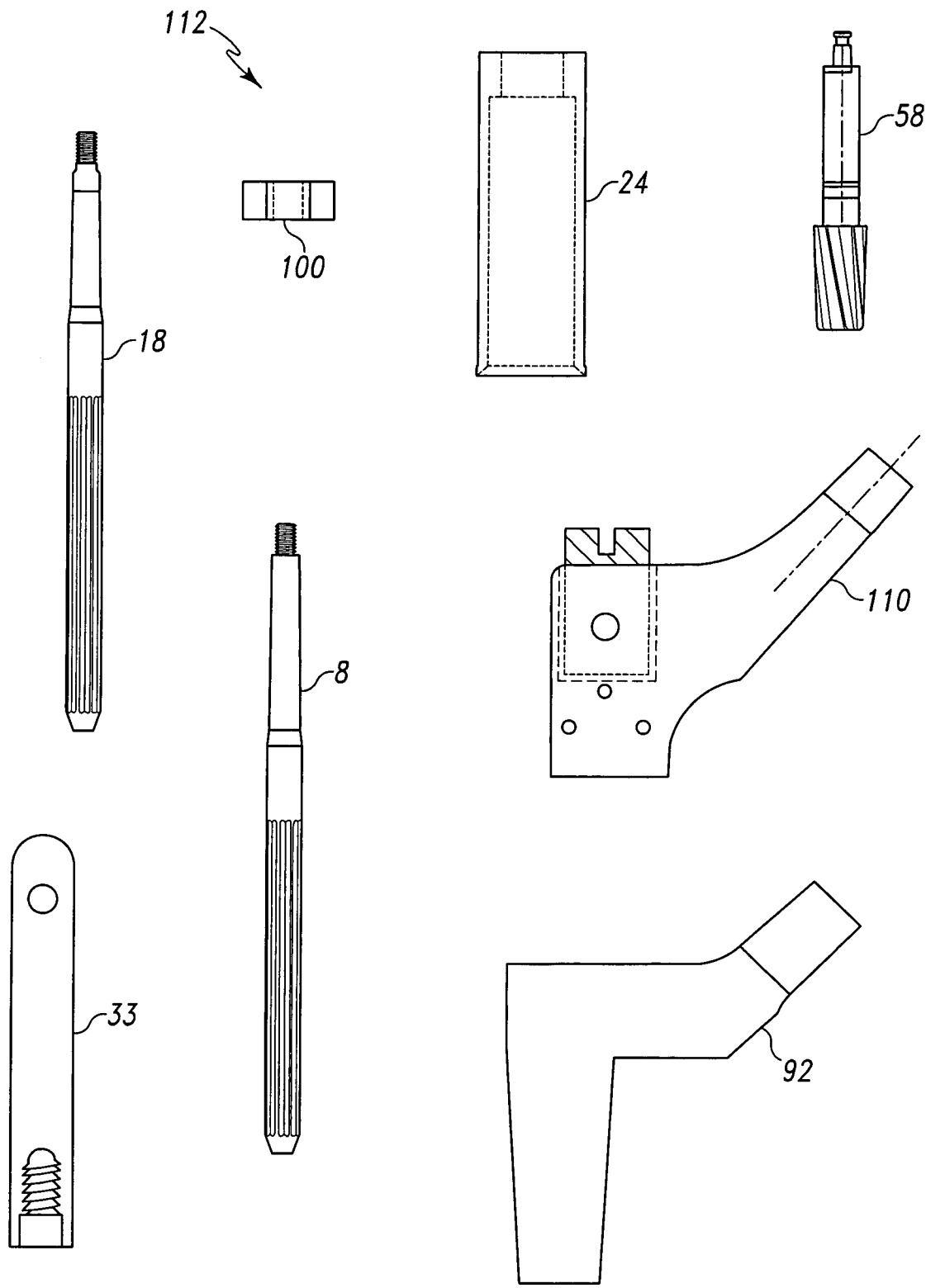
FIG. 16 is a kit for use in performing arthroplasty according to another embodiment of the present invention.

Referring now to FIG. 16, a kit 112 for use in performing arthroplasty is provided. The kit 112 includes proximal reamer 58, as well as, sleeve 24 and distal implant stem 18. The kit 112 may further include a distal reamer 8. The kit 112 may further include a proximal trial 110. The kit 112 may further include proximal implant component 92. The kit 112 may further include guide pin 33.

Figure 17:
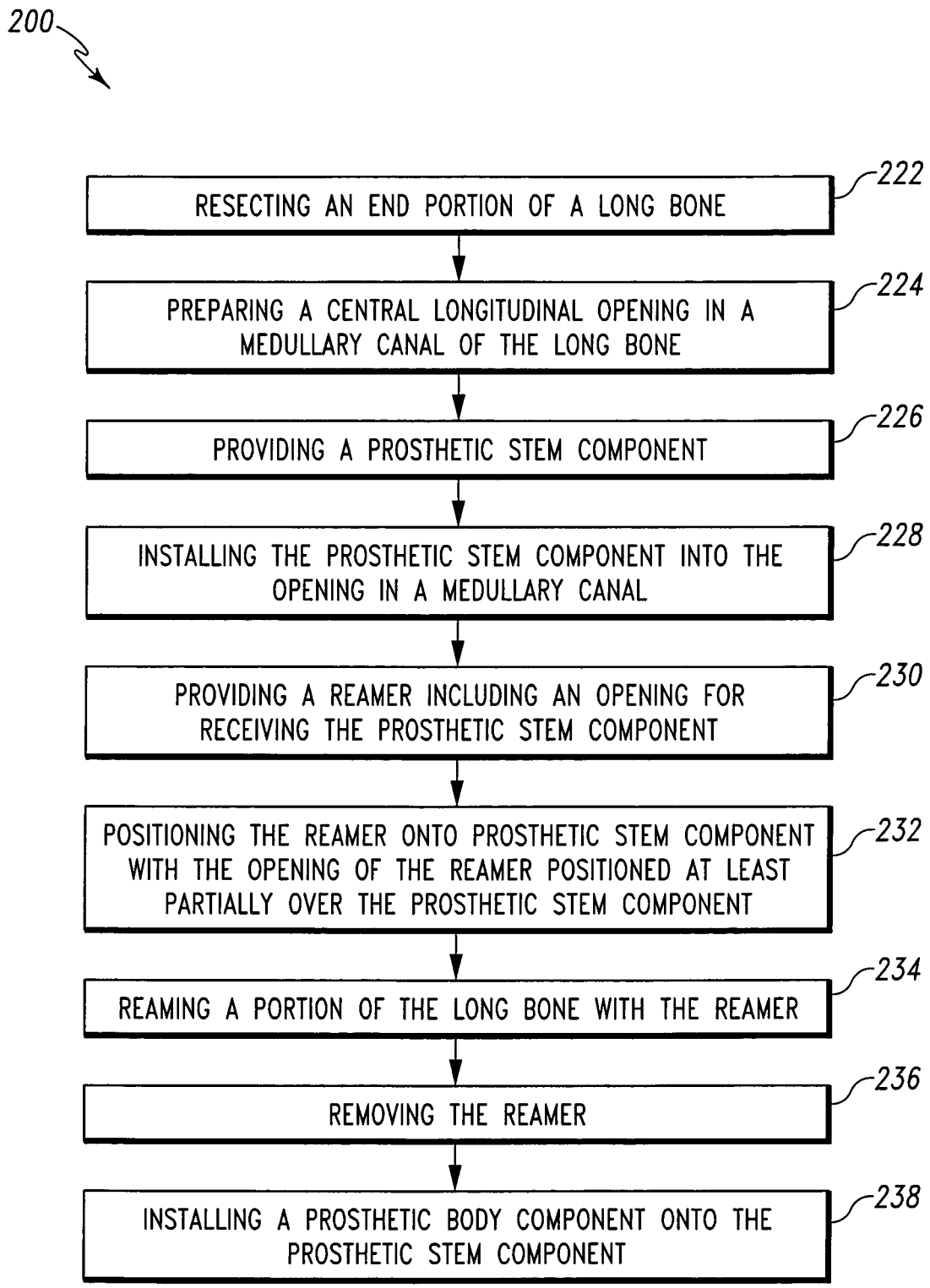
FIG. 17 is a flow chart of a surgical procedure according to another embodiment of the present invention.

According to the present invention and referring now to FIG. 17, a method 220 for performing arthroplasty is provided. The method 220 includes a first step 222 of resecting an end portion of a long bone. The method 220 further includes a second step 224 of preparing a central longitudinal opening in a medullary canal of the long bone. The method 220 further includes a third step 226 of providing a prosthetic stem component and a fourth step 228 of installing the prosthetic stem component into the opening in the medullary canal.

The method 220 further includes a fifth step 230 of providing a reamer including an opening for receiving the prosthetic stem component and a sixth step 232 of positioning the reamer onto prosthetic stem component with the opening of the reamer positioned at least partially over the prosthetic stem component.

The method 220 further includes an seventh step 234 of reaming a portion of the long bone with the reamer and a ninth step 236 of removing the reamer. The method 220 further includes a ninth step 238 of installing a prosthetic body component onto the prosthetic stem component.

Although the present invention and its advantages have been described in detail, it should be understood that various changes, substitutions, and alterations can be made therein without departing from the spirit and scope of the present invention as defined by the appended claims.

We claim:

1. A sleeve for use with an orthopaedic implant stem and a proximal reamer, comprising:
 a bore configured to matingly receive a proximal portion of an orthopaedic implant stem; and
 an outer periphery formed complementary to a cavity in a reamer, wherein
 said sleeve is configured to slidably receive the orthopaedic implant stem,
 said sleeve includes a feature for securing the sleeve to the proximal portion of the orthopaedic implant stem, and
 the bore generally defines a cone shape.

2. The sleeve of claim 1, wherein the cavity of said reamer has a generally cylindrical shape.

3. The sleeve of claim 1, wherein said feature comprises a cavity.

4. The sleeve of claim 1, wherein said feature comprises a protrusion.

* * * * *